United States Patent [19]
Sakakibara et al.

[11] Patent Number: 5,891,702
[45] Date of Patent: Apr. 6, 1999

[54] ATP ELIMINATOR AND THE PROCESS FOR DETERMINING BIOLOGICAL CELLS

[75] Inventors: Tatsuya Sakakibara; Seiji Murakami; Noriaki Hattori; Keiko Yajitate; Teruo Watarai; Motoo Nakajima, all of Noda; Kazuhiro Imai, Tokyo, all of Japan

[73] Assignee: Kikkoman Corporation, Noda, Japan

[21] Appl. No.: 780,161

[22] Filed: Dec. 26, 1996

[30] Foreign Application Priority Data

Dec. 28, 1995 [JP] Japan .................................. 7-352423

[51] Int. Cl.$^6$ .............................. C12N 9/02; C12N 9/14; C12N 9/78; C12Q 1/42
[52] U.S. Cl. .................................. 435/227; 435/4; 435/8; 435/18; 435/21; 435/189; 435/195; 435/232
[58] Field of Search .............................. 435/4, 18, 8, 21, 435/189, 195, 227, 232

[56] References Cited

U.S. PATENT DOCUMENTS

| | | | |
|---|---|---|---|
| 4,650,752 | 3/1987 | Ohashi et al. | 435/15 |
| 5,116,748 | 5/1992 | Takahashi et al. | 435/189 |
| 5,288,613 | 2/1994 | Luong et al. | 435/25 |
| 5,316,907 | 5/1994 | Lurie et al. | 435/4 |
| 5,626,894 | 5/1997 | Bengtsson et al. | 426/62 |

FOREIGN PATENT DOCUMENTS

| | | |
|---|---|---|
| 05304995 | 11/1993 | Japan . |
| 8228761 | 9/1996 | Japan . |
| 94/17198 | 8/1994 | WIPO . |
| 94/28169 | 12/1994 | WIPO . |

OTHER PUBLICATIONS

Bunyatyan et al. Vopr. Biokhim. Mozga, vol. 2, pp. 23–31, Abstract, 1966.

Tapbergenov, S. Ukr. Biokhim. Zh. vol. 41(5), pp. 554–560, Abstract, 1969.

S. Chung et al, "Distribution of ATP Deaminase, and the Purification and Properties of Acid–Type ADP–Deaminating Enzyme" *J. Gen.Appl. Microbiology*, 13, 335–347 (1967).

Jette Klinken et al., "Improvements of luciferin–luciferase methodology for determination of adenylate energy charge ratio of marine samples," Marine Ecology–Process Series, vol. 13, pp. 305–309, 1983.

Bruce McL. Breckenridge, "The Measurement of Cyclic Adenylate in Tissues," Proc. N.A.S., vol. 52, pp. 1580–1586.

W.S. Wilson, et al., "Estimation of Adenine Nucleotides In Brain By Enzymic And Ion–Exchange Chromatographic Methods," Biochemical Pharmacology, vol. 18, pp. 1297–1306.

Atsushi Sugiyama, et al., "An Enzymatic Florometric Assay for Adenosine 3':5'–Monophosphate," Anayltical Biochemestry, 218, pp. 20–25, 1984.

*Primary Examiner*—Leon B. Lankford, Jr.
*Assistant Examiner*—Christopher R. Tate
*Attorney, Agent, or Firm*—Banner & Witcoff, Ltd.

[57] ABSTRACT

The present invention provides a process for eliminating effectively ATP in a sample, using adenosine phosphate deaminase alone or in combination with at least one enzyme selected from the group consisting of apyrase, alkaline phosphatase, acid phosphatase, hexokinase and adenosine triphosphatase, a process for determining biological cells contained in foods and beverages in convenient and precise manner in combination with bioluminescence method, and a reagent for the determination thereof.

3 Claims, 18 Drawing Sheets

SHORT TIME CULTURE PROFILE OF
MODEL-CONTAMINATED KOJI
(VARIOUS GERMS)

KETCHUP

APPLE JUICE

—□— ADDITION OF APYRASE SOLELY IN THE FINAL CONCENTRATION OF 0.05U/ml

—◆— ADDITION OF APYRASE AND ADENOSINE PHOSPHATE DEAMINASE IN THE FINAL CONCENTRATION OF 0.05U/ml, RESPECTIVELY

BEAN CURD

CRAB LEG MEAT LIKE FISH PASTE

─□─ ADDITION OF APYRASE SOLELY IN THE FINAL CONCENTRATION OF 0.05U/ml

─♦─ ADDITION OF APYRASE AND ADENOSINE PHOSPHATE DEAMINASE IN THE FINAL CONCENTRATION OF 0.05U/ml, RESPECTIVELY

ATP ELIMINATOR AND THE PROCESS FOR DETERMINING BIOLOGICAL CELLS

BACKGROUND OF THE INVENTION

1. Field of the Invention

The present invention relates to an eliminator of adenosine-5'-triphosphate (referred to hereinafter as ATP), a process for eliminating ATP therewith, a reagent for measuring biological cells and a process for measuring biological cells therewith.

More particularly, the present invention relates to the evaluation of the biological contamination of samples such as foods and drinks, or the half-products or materials thereof by treating the samples with the ATP eliminator and then measuring ATP in contaminant microorganism cells contained in the samples by the bioluminescence method.

2. Description of Related Art

The measurement of biological cells such as *Escherichia coli*, yeast, and lactic acid bacteria is very important in the fields including food hygiene, biotechnology, clinical laboratory tests, medicine, super pure water and environment.

Biological cells are generally measured by severals methods such as microscopic instrumentation with a hematocytometer (microscopic method), turbidimetry, gravimetry, packed volume measuring method, and colony counting method (referred to hereinafter as pour culture method).

The microscopic method, the turbidimetry, the gravimetry and the packed volume measuring method, however, have disadvantages of low sensitivity or inability to distinguish unviable cells and viable cells, while the pour culture method is not suitable for the cases which are desired to obtain the result quickly since it requires the culture of cells and thus usually requires a period of time for one or more days.

The counting of cells in the aforementioned fields requires the rapid measurement with high sensitivity; the test of microbial contamination of products is essentially required for their shipping in the field of food hygiene. The test has been conventionally carried out by the pour culture method, which requires a period of time for one or more days, so that the products must be stored in a warehouse until the products are guaranteed by the test. This causes not only a problem in the point of logistic efficiency, but also the risk increased of microbial contamination in food products such as milk with the prolonged time of storage. In addition, microorganisms which become an issue for the contamination of foods are generally in a low level, so that a test with high sensitivity is required.

The method for measuring the level of microorganisms which satisfies the requirements described above includes the bioluminescence method of measuring ATP which is present in all of viable microorganisms. This is a method for measuring cells by placing a sample containing the cells into contact with an extraction reagent containing surfactants, trichloroacetic acid (TCA), a Tris-buffer, ethanol or a lytic enzyme to release intracellular ATP out of the cells, placing the ATP into contact with a luminescent reagent which contains luciferin as a substrate of luminescence in a firefly and the enzyme luciferase for producing bioluminescence as a result of the enzyme reaction of luciferin, luciferase and ATP, and measuring the amount of luminescence produced for the determination of the intracellular ATP.

However, ATP is originally present in varying amounts in all of biological cells including not only microorganisms but also unicellular organisms as well as animal and plant tissues in which it is present as the so-called somatic cells. Furthermore, ATP is also present in the free form in the surroundings of biological cells.

Thus, even if it is intended to detect ATP which is contained only in a certain biological cell from a sample containing biological cells, ATP in the biological cells is detected together with free ATP in the neighborhood of the biological cells. In other words, if ATP is intended to be used as an index for the measurement of the biological cells, the free ATP other than that in the biological cells described above is measured as the background luminescence level (noise) together with ATP in the biological cells, and thus such a measurement has a defect of lowering the detection sensitivity of ATP.

As the techniques for eliminating the free ATP, several methods are currently employed including the membrane filter method in which ATP is eliminated from the sample through a membrane filter, the centrifugation method in which it is eliminated by centrifugation, the method for eliminating ATP with an enzyme such as apyrase, adenosine triphosphatase (ATPase), hexokinase, or ATP pyrophosphatase (referred to hereinafter as enzymatic method) (Monthly Food Chemical, SHOKUHIN KAGAKU SHINBUN-SHA, May, 1995, pp. 55–63; Japanese Patent Laid-Open Publication No. 65800/1990; U.S. Pat. No. 5,316,907; Analitical Biochemistry, 218, 20–25, 1994; Bulletin of the Japanese Society of Scientific Fisheries, 52 (9), 1695, 1986; PROC. N.A.S. Vol 52, 1580–1586, 1964; PCT WO 94/28169; and Marine Ecology-Progress Series, 13, 305–309, 1983).

The membrane filter method has however disadvantages in that it is complicated in operation, inferior in filtration ability and insufficient of the ATP eliminating effect.

The centrifugation method also has a disadvantage in that it is complicated in operation and solid components in samples are sedimented and separated together with bacteria, so that it cannot realize the measurement at high precision.

Furthermore, the enzymatic method has also a disadvantage in that it is difficult to lower the background due to the sample, and the ATP eliminating effect remains in unsatisfactory levels.

SUMMARY OF THE INVENTION

The object of the present invention is to provide a novel process for eliminating ATP which permits free ATP from a sample containing biological cells at a minimal level, and to provide a process for measuring the biological cells at a high precision by the process for eliminating ATP in combination with the bioluminescence method.

DETAILED DESCRIPTION OF THE INVENTION

Figure 1:
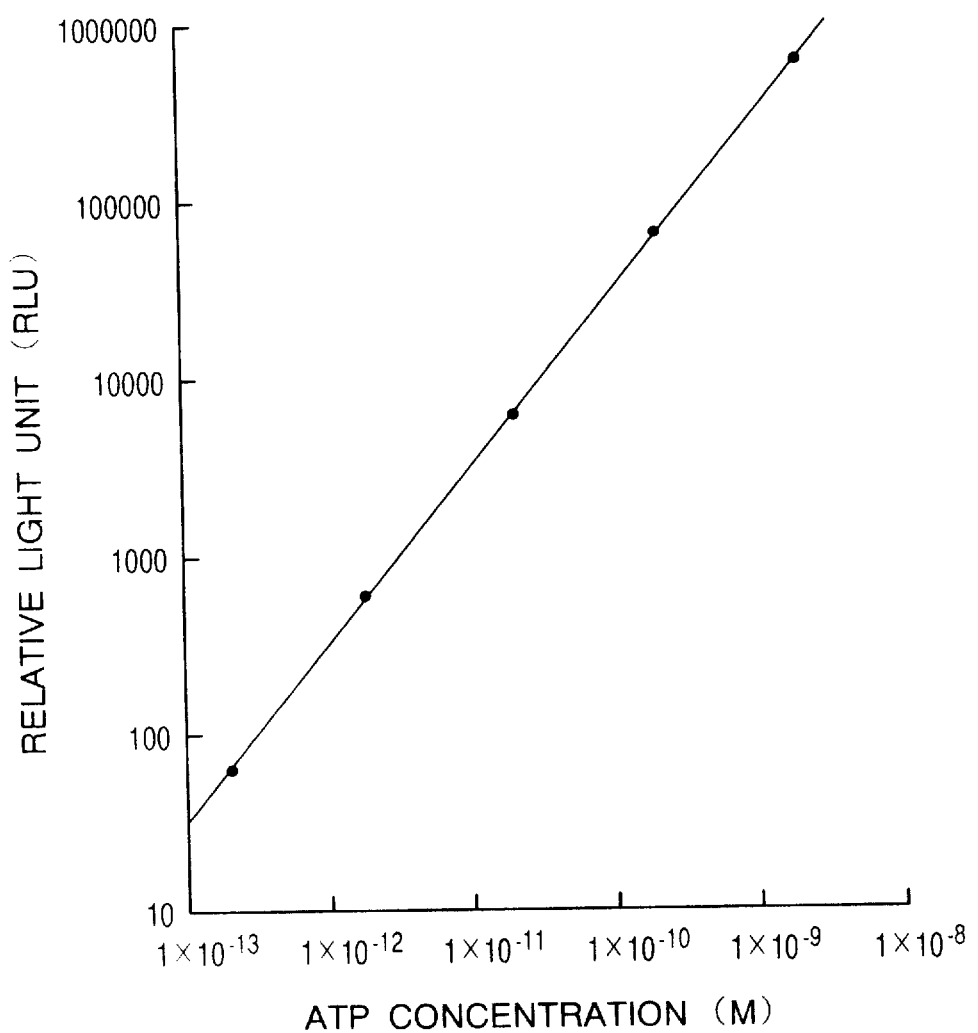
FIG. 1 illustrates a calibration curve of ATP with a luminometer "Lumat LB9501" manufactured by Berthold.

The present inventors have earnestly carried out investigation in order to settle the aforementioned problems. As a result, they have found that ATP contained in a sample can be eliminated to a minimal level by using adenosine phosphate deaminase alone or in combination with at least one of those selected from the group consisting of apyrase, alkaline phosphatase, acid phosphatase, hexokinase and adenosine triphosphatase.

Furthermore, they have also found that the combination of the ATP eliminating method and the bioluminescence method can realize precisely the estimation of biological cells by eliminating free ATP other than that in biological cells to remove the influence due to the background luminescence (noise) level and measuring ATP alone contained in the biological cells.

In other words, (1) the present invention is an ATP eliminating agent which comprises adenosine phosphate deaminase as an effective ingredient; (2) a background ATP eliminator in ATP bioluminescence method which comprises containing adenosine phosphate deaminase as an effective ingredient; (3) the present invention is an ATP eliminating agent which comprises at least one of those selected from the group consisting of apyrase, alkaline phosphatase, acid phosphatase, hexokinase and adenosine triphosphatase, and adenosine phosphate deaminase as the effective ingredients; (4) a background ATP eliminator in ATP bioluminescence method which comprises containing at least one member selected from the group consisting of apyrase, alkaline phosphatase, acid phosphatase, hexokinase and adenosine triphosphatase, and adenosine phosphate deaminase as effective ingredients; (5) the present invention is a process for eliminating ATP comprising the addition of adenosine phosphate deaminase to an ATP containing sample; (6) the present invention is a process for eliminating ATP comprising the addition of at least one of those selected from the group consisting of apyrase, alkaline phosphatase, acid phosphatase, hexokinase and adenosine triphosphatase, in combination with adenosine phosphate deaminase to an ATP containing sample; (7) the present invention is a reagent for measuring biological cells which comprises adenosine phosphate deaminase as an effective ingredient; (8) the present invention is a reagent for measuring biological cells which comprises at least one of those selected from the group consisting of apyrase, alkaline phosphatase, acid phosphatase, hexokinase and adenosine triphosphatase, and adenosine phosphate deaminase as the effective ingredients; (9) the present invention is a process for measuring biological cells which comprises eliminating free ATP in a sample containing the biological cells by treating the cells with adenosine phosphate deaminase and then measuring ATP in the biological cells by the bioluminescence method; and (10) the present invention is a process for measuring biological cells which comprises eliminating free ATP in a sample containing the biological cells by treating the cells with at least one of those selected from the group consisting of apyrase, alkaline phosphatase, acid phosphatase, hexokinase and adenosine triphosphatase, and adenosine phosphate deaminase, and then measuring ATP in the biological cells by the bioluminescence method.

The present invention is now described in detail below.

Adenosine phosphate deaminase used herein is an enzyme which is also designated adenine nucleotide deaminase. Furthermore, the enzyme is registered as "Enzyme Classification (referred to hereinafter as E.C.) E.C.3.5.4.17".

This enzyme is the one for catalyzing deamination reaction which acts, as opposed to AMP deaminase (E.C.3.5.4.6) specifically acting on AMP or adenosine deaminase (E.C.3.5.4.4) specifically acting on adenosine, on a wide variety of substrates such as ATP, adenosine diphosphate (referred to hereinafter as ADP), adenosine monophosphate (referred to hereinafter as AMP), adenosine, and cyclic AMP regardless of phosphate groups.

This enzyme catalyzes the production of inosine triphosphate (referred to hereinafter as ITP) on the use of ATP as a substrate, inosine diphosphate (referred to hereinafter as IDP) on the use of ADP as a substrate, and inosine monophosphate (referred to hereinafter as IMP) on the use of AMP as a substrate (see, Shiro Akahori "ENZYME HANDBOOK", Asakura Shoten, Dec. 1, 1982, p. 611; Shigeaki Baba et al. Ed., "CLINICAL ENZYME HANDBOOK", Kodansha, Sep. 10, 1982, p. 55; The Journal of General and Applied Microbiology, 13, 335–347, 1967); and Agricultural and Biological Chemistry, 29 (6), 508–514, 1965).

It has been found that ATP deaminase (E.C.3.5.4.18) has a similar substrate specificity to adenosine phosphate deaminase (see, "ENZYME HANDBOOK", ditto, p. 611; and The Journal of Biochemistry, 61 (1), 1–9, 1967).

Thus, the term adenosine phosphate deaminase herein means adenosine phosphate deaminase and ATP deaminase.

Apyrase (E.C.3.6.1.5) used in the present invention is an enzyme which catalyzes the dephosphorylation of ATP, ADP, ITP, and IDP (see "ENZYME HANDBOOK", ditto, p. 617).

Adenosine triphosphatase (E.C.3.6.1.3) is an enzyme which catalyzes the dephosphorylation of ATP (see "ENZYME HANDBOOK", ditto, p. 616).

Hoxokinase (E.C.2.7.1.1) is an enzyme which catalyzes the production D-hexose-6-phosphate by the rearrangement of the phosphate moiety in adenosine triphosphate to D-hexose (see "ENZYME HANDBOOK", ditto, p. 330).

Phosphatase is an enzyme including acid phosphatase (E.C.3.1.3.2) and alkaline phosphatase (E.C.3.1.3.1) and catalyzing dephosphorylation (see "ENZYME HANDBOOK", ditto, p. 434–435).

5'-nucleotidase (E.C.3.1.3.5) is an enzyme which catalyzes the hydrolysis of 5'-ribonucletide or 5'-deoxyribonucleotide to yield nucleotide and phosphate (see "ENZYME HANDBOOK", ditto, p. 436).

The present invention can be practiced by adding to a sample containing ATP adenosine phosphate deaminase alone or the enzyme in combination with at least one of those selected from the group consisting of apyrase, alkaline phosphatase, acid phosphatase, hexokinase and adenosine triphosphatase.

The ATP eliminator used in the present invention includes the one which comprises adenosine phosphate deaminase as an effective ingredient or the enzyme and at least one of those selected from the group consisting of apyrase, alkaline phosphatase, acid phosphatase, hexokinase and adenosine triphosphatase as effective ingredients.

The process for measuring biological cells according to the present invention is carried out by mixing a sample containing biological cells such as bacteria, e.g. *E. coli*, microbial cells of yeast, lactic acid bacteria and the like, and animal and plant cells with adenosine phosphate deaminase alone or in combination with at least one of those selected from the group consisting of apyrase, alkaline phosphatase, acid phosphatase, hexokinase and adenosine triphosphatase to eliminate free ATP in the sample, and then measuring the concentration of ATP in the biological cells by the bioluminescence method.

Specific examples of the samples containing the aforementioned biological cells include samples containing any biological cells in the measurements of the end point of microbial mortality in food and drink manufacturing industry, clinical test industry, pharmaceutical manufacturing industry, effluent treatment industry, microbial test, anti-bacterial test, resistance test, the measurement of MIC, and the hygiene test by the smear method.

Samples containing biological cells in food and drink include food and drink products, half-products thereof or materials thereof. Specific examples include pastes of fishery product and live-stock products such as ham; beverages such as apple juice, tomato juice and milk; processed products of plant protein such as bean curd; processed products of fruits and vegetables such as tomato ketchups; brewed products such as soy sauce, bean paste, rice wine, wine and vineger; seasonings such as Worcester sauce, sauce containing soy sauce and vineger, sauce, broth and dressing; sweetened breads; noodles such as udon and buckwheat noodles; processed products of cereals such as boiled rice; and microbial culturing products and processing products thereof such as soy sauce koji and yeast extract.

The sample in the form of liquid is taken out in a certain amount and directly used for the measurement, while the one in the form of solid is taken out in a certain amount, mixed with sterile distilled water, and homogenized in a grinder, a masticator or a stomacher. Alternatively, the mixture is contact stirred vigorously, and the liquid portion is recovered as a sample for the measurement.

Adenosine phosphate deaminase added to the sample containing biological cells is preferably in the final concentration of 0.001 U/ml or more, particularly 0.01–0.1 U/ml.

Apyrase is added preferably in the final concentration of 0.001 U/ml or more, particularly 0.01–0.2 U/ml.

Each of alkaline phosphatase, acid phosphatase, hexokinase and adenosine triphosphatase is preferably added to the sample in the final concentration of 0.001 U/ml or more, particularly 0.01–50 U/ml.

The enzyme reaction is preferably carried out at a pH in a weak acidic—weak alkaline range.

For instance, when adenosine phosphate deaminase is employed alone or in combination with apyrase, the reaction is preferably carried out at a pH in the range of 5.0–8.0.

The sample is adjusted to a desired pH with a phosphate buffer, a HEPES buffer, or a MES buffer.

The enzyme reaction time, which depends to some extent on the kinds and properties of samples containing biological cells, pHs during the reaction, the concentrations of enzymes added, and the reaction temperatures, is preferably within about 2 hours, particularly 1–30 minutes. If the reaction is continued excessively long, biological cells cannot be counted precisely and the precision and reliability of measurements will be impaired due to the proliferation of microorganisms contained in the sample during the reaction.

The enzyme reaction is preferably carried out at a temperature of 30°–50° C., particularly 40°–45° C. When it is intended only to eliminate ATP, it is preferred to carry out the reaction at the temperature range described above. However, when the reaction is contemplated on a sample containing biological cells, it is preferred to carry out the reaction at the temperature range in which the cells are not extinguished, i.e. from room temperature to 40° C. in order to avoid the risk of extinction of the biological cells at an excessively high temperature.

The reagent for measuring biological cells according to the present invention is prepared in such a manner that the final concentration of adenosine phosphate deaminase alone or in combination with at least one of those selected from the group consisting of apyrase, alkaline phosphatase, acid phosphatase, hexokinase and adenosine triphosphatase in the reaction solution is in range of the concentrations of the following effective ingredients.

The preferred concentrations of the enzymes used in combination are as follows:

adenosine phosphate deaminase: at the final concentration of 0.001 U/ml or more, particularly 0.01–0.1 U/ml;

apyrase: at the final concentration of 0.001 U/ml or more, particularly 0.01–0.2 U/ml;

alkaline phosphatase: at the final concentration of 0.001 U/ml or more, particularly 0.01–50 U/ml;

acid phosphatase: at the final concentration of 0.001 U/ml or more, particularly 0.01–50 U/ml;

hexokinase: at the final concentration of 0.001 U/ml or more, particularly 0.01–50 U/ml;

adenosine triphosphatase: at the final concentration of 0.001 U/ml or more, particularly 0.01–50 U/ml.

The calibration curve of ATP used in examples was prepared by the following procedure.

The measurement of ATP is carried out by adding a luciferin-luciferase containing luminescent reagent to an ATP containing sample and quantitatively determining the amount of bioluminescence released.

The reagent kit for measuring ATP as a luminescence amount with the luciferin-luciferase containing luminescent reagent and the apparatus for measuring the luminescence amount are commercially available, and the present invention can be carried out with the commercially available kit and apparatus to measure ATP contained in a subject microorganism as a luminescence amount.

An example of the luciferin-luciferase containing luminescent reagent (reagent for measuring ATP) is illustrated below (see BUNSEKI KAGAKU, 44 (10), 845–851, particularly 846 (1995)).

10 mM magnesium sulfate (Mg ion), 0.30 mM D-luciferin (luminescent material), 1.0 mM EDTA (stabilizer), 1.0 mM dithiothreitol (stabilizer), 0.51 mg/ml luciferase (from Genji firefly) (luminescent enzyme), 0.2% bovine serum albumin (BSA) (stabilizer), in 50 mM HEPES buffer (pH 7.8).

The exemplary preparation of the calibration curve of ATP with a luminometer "Lumat LB9501" manufactured by Berthold is described below.

Super pure water (100 $\mu$l) was added to 100 $\mu$l of an ATP standard solution having a known concentration, followed by 100 $\mu$l of a luciferin-luciferase containing luminescent reagent (referred to hereinafter as luminescent reagent) in order to estimate the relative light Unit S by the measurement of luminescence with waiting for one second before integration for three seconds with the luminometer LB9501.

At the same time, 100 $\mu$l of a luciferin-luciferase containing luminescent reagent (referred to hereinafter as luminescent reagent) was added to 200 $\mu$l of super pure water in order to carry out the measurement of luminescence for estimate the luminescence amount R in the same manner as above, and the measurement R was used as the blank.

The difference S–R gives the net amount of luminescence of ATP (Z), and a calibration curve of ATP was prepared by setting the Y axis of the coordinates as the net amount of luminescence Z and the X axis as the ATP concentration (M=mole/l) as shown in FIG. 1.

Next, the enzymes used in examples of the present invention and the method for measuring their enzyme activities are shown below.

(Enzyme solutions to be used)

(a) Adenosine phosphate deaminase (derived from Aspergillus genus), 5 U/ml

Method for measuring the activity: ATP was added to a 100 mM sodium acetate buffer containing EDTA, pH 5.0, to obtain 80 $\mu$M ATP solution, which was used as a substrate solution. A 100 $\mu$l portion of an enzyme solution was added to 3 ml of the substrate solution to start the reaction at 30° C. for 30 minutes. A 100 $\mu$l portion of a 60% perchloric acid was added to the mixture to stop the reaction, and the optical density (OD) of the mixture was measured at 265 nm.

And the amount of the enzyme which catalyzes the variation of OD of 2.4 per minute was regarded as 1 unit (U).

(b) Apyrase grade VIII (from potato) (Sigma), 5 U/ml

Method for measuring the activity: The amount of the enzyme which catalyzes the release of 1.0 $\mu$mole inorganic phosphoric acid from ATP per minute under the condition of pH 5 and 30° C. was regarded as 1 unit.

(c) Acid phosphatase type VII (from white potato) (Sigma) 250 U/ml

Method for measuring the activity: The amount of the enzyme which catalyzes the hydrolysis of 1.0 $\mu$mole p-nitrophenyl phosphate per minute under the condition of pH 4.8 and 37° C. was regarded as 1 unit.

(d) Adenosine deaminase type V (from bovine spleen) (Sigma) 250 U/ml

Method for measuring the activity: The amount of the enzyme which catalyzes the deamination of 1.0 $\mu$mole adenosine to form inosine per minute under the condition of pH 7.5 and 25° C. was regarded as 1 unit.

(e) 5'-nucleotidase (from crotalus adamanteus venom) (Sigma) 250 U/ml

Method for measuring the activity: The amount of the enzyme which catalyzes the hydrolysis of adenosine-5'-monophosphate at pH 9.0 and 37° C. to release 1.0 μmole inorganic phosphoric acid per minute was regarded as 1unit.

(f) AMP deaminase (from rabbit muscle) (Sigma) 25.5 U/ml
Method for measuring the activity: The amount of the enzyme which catalyzes the deamination of 1.0 μmole 5'-adenosine monophosphate per minute under the condition of pH 6.5 and 25° C. was regarded as 1 unit.

(g) Adenosine triphosphatase (from porcine cerebral cortex) (Sigma) 5 U/ml
Method for measuring the activity: The amount of the enzyme which catalyzes the release of 1.0 μmole inorganic phosphoric acid from ATP per minute in the presence of $Na^+$, $K^+$ and $Mg^{2+}$ under the condition of pH 7.8 and 37° C. was regarded as 1 unit.

(h) Alkaline phosphatase (from bovine intestinal mucosa) (Sigma) 250 U/ml
Method for measuring the activity: The amount of the enzyme which catalyzes the hydrolysis of 1.0 μmole p-nitrophenyl phosphate per minute under the condition of pH 9.8 and 37° C. was regarded as 1 unit.

(i) Hexokinase (from yeast) (Boehringer-Mannheim) 50 U/ml
Method for measuring the activity: The amount of the enzyme which catalyzes the rearrangement 1.0 μmole of phosphate in ATP to glucose per minute under the condition of pH 7.6 and 25° C. was regarded as 1 unit.

The present invention is now described in more detail with reference to examples.

EXAMPLE 1

An example of eliminating ATP by mixing yeast extract containing ATP with adenosine deaminase alone or in combination with at least one of those selected from the group consisting of apyrase, alkaline phosphatase, acid phosphatase, hexokinase and adenosine triphosphatase.

Yeast extract powder (1 g) (Difco) was dissolved in 100 ml of 20 mM HEPES buffer (pH 6.8) to prepare 1% (w/v) yeast extract (pH 6.8).

This solution, which was sterilized by filtration through a membrane filter (MILLEX-GS, pore size: 0.22 μm, Millipore), was used as the sample solution, which was divided into 19 of 5 ml portions, and to the first portion (control) was added 50 μl of super pure water, to the second portion (the present invention 1) was added 50 μl of an adenosine phosphate deaminase enzyme solution (final concentration, 0.05 U/ml), to the third portion (the present invention 2) were added 50 μl of an adenosine phosphate deaminase enzyme solution and 50 μl of an apyrase enzyme solution (final concentration, 0.05 U/ml, respectively), to the fourth portion (the present invention 3) were added 50 μl of an adenosine phosphate deaminase enzyme solution, 50 μl of an apyrase enzyme solution and 50 μl of an acid phosphatase enzyme solution (final concentration, 0.05 U/ml, 0.05 U/ml and 2.5 U/ml, respectively), to the fifth portion (the present invention 4) were added 50 μl of an adenosine phosphate deaminase enzyme solution, 50 μl of an adenosine triphosphatase enzyme solution (final concentration, 0.05 U/ml, respectively), to the sixth portion (the present invention 5) were added 50 μl of an adenosine phosphate deaminase enzyme solution, and 50 μl of a hexokinase enzyme solution (final concentration, 0.05 U/ml and 0.5 U/ml, respectively), to the seventh portion (the present invention 6) were added 50 μl of an adenosine phosphate deaminase enzyme solution, and 50 μl of an alkaline phosphatase enzyme solution (final concentration, 0.05 U/ml and 2.5 U/ml, respectively), to the eighth portion (the present invention 7) were added 50 μl of an adenosine phosphate deaminase enzyme solution, and 50 μl of an acid phosphatase enzyme solution (final concentration, 0.05 U/ml and 2.5 U/ml, respectively), to the ninth portion (comparative example 1) as added 50 μl of an apyrase enzyme solution (final concentration, 0.05 U/ml), to the tenth portion (comparative example 2) was added 100 μl of an apyrase enzyme solution (final concentration, 0.10 U/ml), to the eleventh portion (comparative example 3) were added 50 μl of an apyrase enzyme solution, and 50 μl of a 5'-nucleotidase enzyme solution (final concentration, 0.05 U/ml and 2.5 U/ml, respectively), to the twelfth portion (comparative example 4) were added 50 μl of an apyrase enzyme solution, 50 μl of a 5'-nucleotidase enzyme solution, and 50 μl of an adenosine deaminase enzyme solution (final concentration, 0.05 U/ml, 2.5 U/ml and 2.5 U/ml, respectively), to the thirteenth portion (comparative example 5) were added 50 μl of an apyrase enzyme solution, and 50 μl of an acid phosphatase enzyme solution (final concentration, 0.05 U/ml, and 2.5 U/ml, respectively), to the fourteenth portion (comparative example 6) were added 50 μl of an apyrase enzyme solution, 50 μl of an acid phosphatase enzyme solution, and 50 μl of an adenosine deaminase enzyme solution (final concentration, 0.05 U/ml, 2.5 U/ml and 2.5 U/ml, respectively), to the fifteenth portion (comparative example 7) were added 50 μl of an apyrase enzyme solution, and 50 μl of an AMP deaminase enzyme solution (final concentration, 0.05 U/ml, and 0.255 U/ml, respectively), to the sixteenth portion (comparative example 8) was added 50 μl of an adenosine triphosphatase enzyme solution (final concentration, 0.05 U/ml), to the seventeenth portion (comparative example 9) was added 50 μl of a hexokinase enzyme solution (final concentration, 0.5 U/ml), to the eighteenth portion (comparative example 10) was added 50 μl of an alkaline phosphatase enzyme solution (final concentration, 2.5 U/ml), and to the nineteenth portion (comparative example 11) was added 50 μl of an acid phosphatase enzyme solution (final concentration, 2.5 U/ml).

Each of the mixtures was subjected to reaction at 30° C., and portions were taken out with the passage of time to measure the luminescence.

Method for Measuring Luminescence

Super pure water (100 μl) was added to 100 μl of the sample taken out, followed by 100 μl of a luciferin-luciferase containing luminescent reagent (referred to hereinafter as luminescent reagent) in order to estimate the relative luminescence amount S by the measurement of luminescence with waiting for one second before integration for three seconds with the luminometer LB9501.

At the same time, a luminescence amount was measured in the same manner as described above except that "100 μl of super pure water" was used in place of "the sample taken out", and the measurement was used as the blank R of the luminescent reagent.

The difference S–R gives the net amount of luminescence A.

The luciferin-luciferase luminescent reaction is inhibited somewhat by the ingredients in the sample, and the amount of luminescence A obtained is only an apparent value. The amount of luminescence A should be corrected as follows.

That is, the luminescent coefficient K is obtained according to the following equation, and the amount of luminescence A is divided by the luminescent coefficient K to obtain the corrected value Y (net amount of luminescence). Next, the net concentration of ATP was obtained with use of the calibration curve of the concentration of ATP corresponding to the corrected values Y which had been preliminarily prepared (FIG. 1). (The corrected amounts of luminescence in examples described below were also obtained in the same manner as above.)

Figure 2:
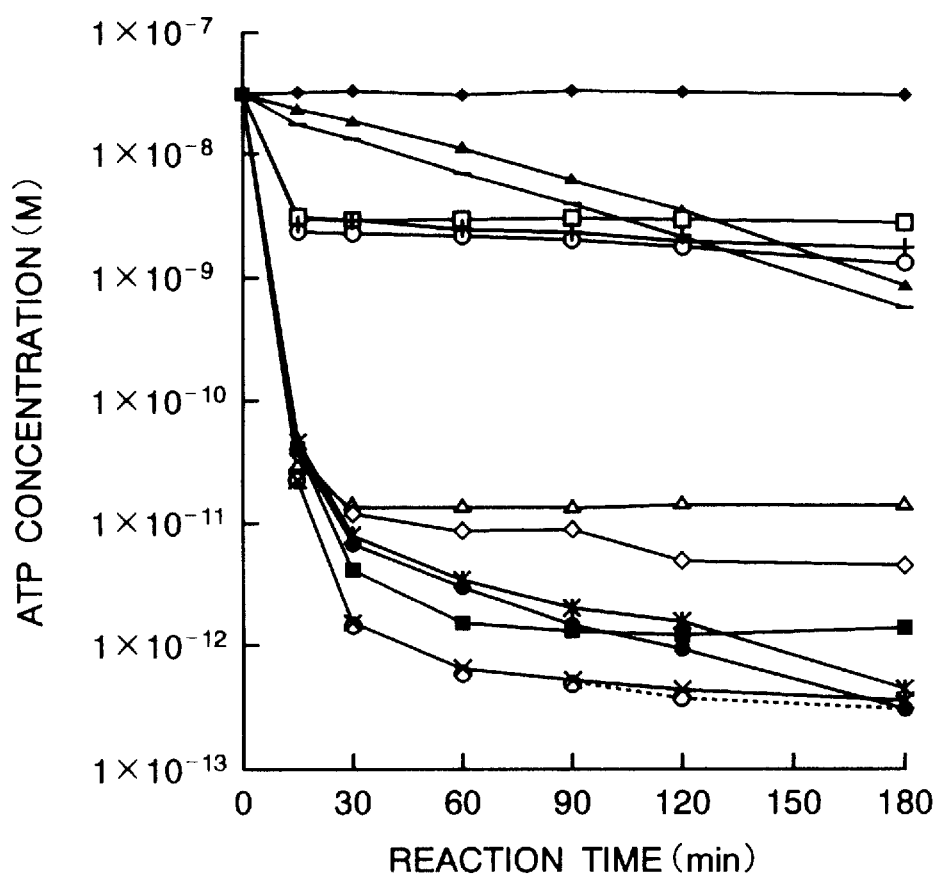
FIG. 2 illustrates the relationship between the period of enzyme reaction and the concentration of ATP remaining after the reaction in the method for eliminating ATP with an enzyme.
—◆— Control,
—□— Apyrase, 0.05 U/ml (Comparative Example 1),
—□— Apyrase, 0.10 U/ml (Comparative Example 2),
—□— Apyrase+5'-nucleotidase (Comparative Example 3),
—□— Apyrase+5'-nucleotidase+adenosine deaminase (Comparative Example 4),
—○— Apyrase+acid phosphatase (Comparative Example 5), —|— Apyrase+acid phosphatase+adenosine deaminase (Comparative Example 6),
—□— Apyrase+AMP deaminase (Comparative Example 7),
—□— Adenosine triphosphatase (Comparative Example 8),
—□— Hexokinase (Comparative Example 9),
—▲— Alkaline phosphatase (Comparative Example 10),
— Acid phosphatase (Comparative Example 11),
—△— Adenosine phosphate deaminase (The Present Invention 1),
—x— Adenosine phosphate deaminase+apyrase (The Present Invention 2),
---○--- Adenosine phosphate deaminase+apyrase+acid phosphatase (The Present Invention 3),
—◇— Adenosine phosphate deaminase+adenosine triphosphatase (The Present Invention 4),
—■— Adenosine phosphate deaminase+hexokinase (The Present Invention 5),
—*—Adenosine phosphate deaminase+alkaline phosphatase (The Present Invention 6),
—●— Adenosine phosphate deaminase+acid phosphatase (The Present Invention 7).

The results are shown in FIG. 2.

Method for calculating the corrected amount of luminescence

Y (corrected value of luminescence)=A (apparent value) /K (luminescent coefficient), K (luminescent coefficient)=[H (internal standard value) –A (apparent value)]/G (real standard value), H: a value obtained by measuring luminescence by adding to a 100 μl portion of each of the samples taken out with the passage of time 100 μl of the ATP standard solution ($2 \times 10^{-9}$ mole/l (referred to hereinafter as M)), followed by 100 μl of the luciferin-luciferase containing luminescent reagent (internal standard value);

A: a value obtained by measuring luminescence by adding to a 100 μl portion of each of the samples 100 μl of the super pure water, followed by 100 μl of the luciferin-luciferase containing luminescent reagent (apparent value);

G: a value obtained by measuring luminescence by adding to a 100 μl of super pure water 100 μl of the ATP standard solution ($2 \times 10^{-9}$M), followed by 100 μl of the luciferin-luciferase containing luminescent reagent (real standard value);

K: luminescent coefficient;

Y: corrected luminescent value (net measurement of luminescence).

It has been revealed from the result in FIG. 2 that in either of Comparative Example 1 in which the apyrase enzyme solution was added so as the final concentration to be 0.05 U/ml, Comparative Example 2 in which the same enzyme solution was added so as the final concentration to be 0.10 U/ml, Comparative Example 3 in which the combination of apyrase and 5'-nucleotidase was added, Comparative Example 4 in which the combination of apyrase, 5'-nucleotidase and adenosine deaminase was added, Comparative Example 5 in which the combination of apyrase and acid phosphatase was added, Comparative Example 6 in which the combination of apyrase, acid phosphatase and adenosine deaminase was added, Comparative Example 7 in which the combination of apyrase and AMP deaminase was added, Comparative Example 8 in which adenosine triphosphatase was added, Comparative Example 9 in which hexokinase was added, Comparative Example 10 in which alkaline phosphatase was added, and Comparative Example 11 in which acid phosphatase was added, the concentration of ATP in the yeast extract was unsatisfactorily decreased at most to about 1/10–about 1/100 times of the initial concentration of ATP ($10^{-9}$M).

As opposed to this, The Present Invention 1 in which adenosine phosphate deaminase was added alone can decrease the concentration of ATP to about one-several thousandth times of the initial concentration of ATP ($10^{-11}$M).

It has been revealed that in either of The Present Invention 2 in which the combination of adenosine phosphate deaminase and apyrase was added, The Present Invention 3 in which the combination of adenosine phosphate deaminase, apyrase and acid phosphatase was added, The Present Invention 6 in which the combination of adenosine phosphate deaminase and alkaline phosphatase was added, and The Present Invention 7 in which the combination of adenosine phosphate deaminase and acid phosphatase was added, the concentration of ATP can be reduced to about one hundred-thousandth times of the initial concentration of ATP ($10^{-13}$M). It is also understood that in The Present Invention 4 in which the combination of adenosine phosphate deaminase and adenosine triphosphatase was added, the concentration of ATP can be reduced to about one ten-thousandth times of the initial concentration of ATP, and in The Present Invention 5 in which the combination of adenosine phosphate deaminase and hexokinase was added, the concentration of ATP can be reduced to about one several ten-thousandth times of the initial concentration of ATP ($10^{-12}$M).

EXAMPLE 2

An example for obtaining the optimal concentration of adenosine phosphate deaminase on eliminating free ATP present in a yeast extract by adding the combination of adenosine phosphate deaminase and apyrase to the extract.

Yeast extract powder (Difco) was dissolved in 1 mM HEPES buffer (pH 6.8) to prepare a 1% (w/v) yeast extract (pH 6.8) solution, which was sterilized by filtration through a membrane filter (MILLEX-GS, pore size: 0.22 μm, Millipore) to prepare a sterile yeast extract.

Figure 3:
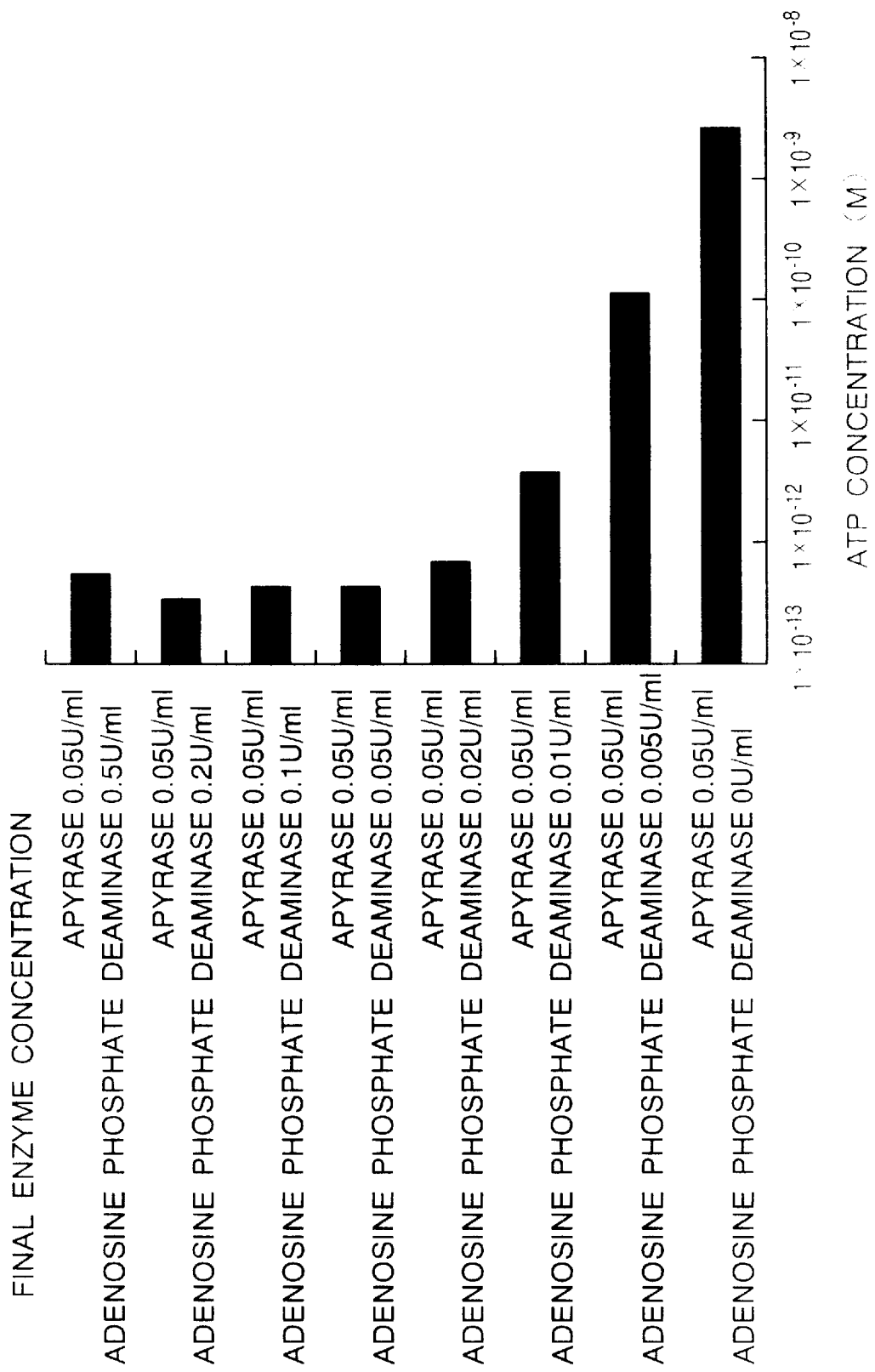
FIG. 3 illustrates the relationship between the activity of adenosine phosphate deaminase and the concentration of ATP remaining after the reaction in the method for eliminating ATP with adenosine phosphate deaminase in combination with apyrase.

This solution was divided into 8 of 5 ml portions, and to each of the first—seventh portions were added adenosine phosphate deaminase and apyrase so that the solution has the final enzyme concentrations as shown in FIG. 3, while to the eighth portion for comparison was added only apyrase but not adenosine phosphate deaminase so that the solution has the final enzyme concentration as shown in FIG. 3. Each of the sample solutions was subjected to reaction at 37° C. for 90 minutes to eliminate free ATP in the yeast extract, and the luminescence of the sample thus obtained was measured by the following method.

The measurement of the luminescence was carried out in the same manner as in Example 1 to obtain the ATP concentration. The result is shown in FIG. 3.

It has been revealed from the result in FIG. 3 that in the portion having added thereto only apyrase but not adenosine phosphate deaminase, the concentration of ATP can be reduced to a level of about $10^{-9}$M, while in the portions having added thereto the combination of apyrase and adenosine phosphate deaminase, the concentration of ATP can be further reduced. The concentration of ATP can be further reduced as the concentration of adenosine phosphate deaminase is increased. It can be seen that the final concentration of adenosine phosphate deaminase is preferably in the range of 0.01 U/ml or more.

EXAMPLE 3

Free ATP in the yeast extract is first eliminated with the combination of adenosine phosphate deaminase and apyrase, and an ATP extracting agent containing a certain concentration of ATP is then added in the presence of both enzyme activities. The mixture is maintained for a time which is required generally for the extraction of ATP, e.g. for 20 seconds before measurement of the residual ATP. This makes it possible to estimate the amount of disruptive elimination of ATP extracted from biological cells. It is also possible to determine the optimal concentration of adenosine phosphate deaminase or apyrase.

Figure 4:
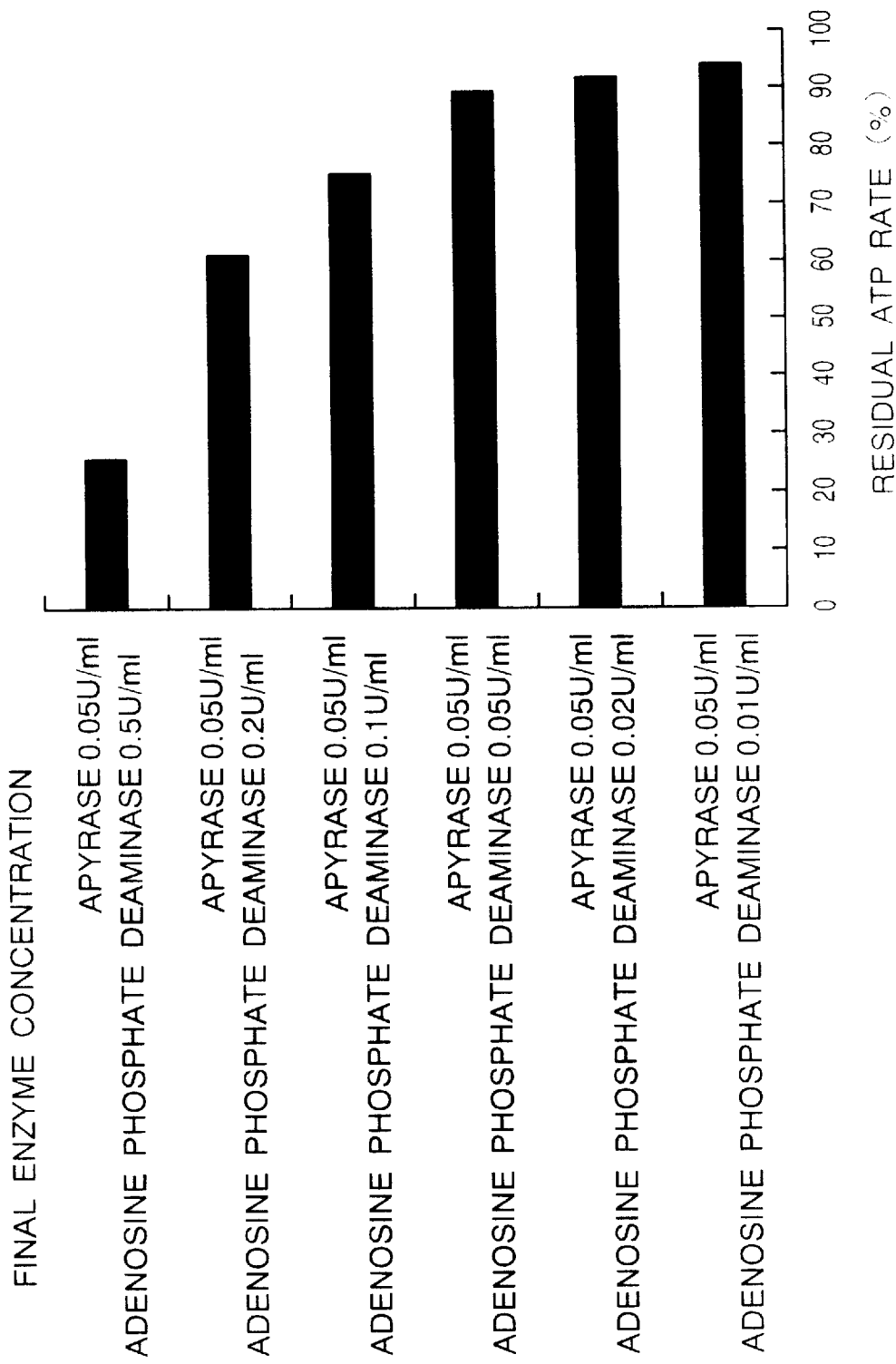
FIG. 4 illustrates the relationship between the activity of adenosine phosphate deaminase and the ratio of the remaining ATP in the method for eliminating ATP with adenosine phosphate deaminase in combination with apyrase.

In the same manner as in Example 2, sterile yeast extract was divided into 6 of 5 ml portions, and to each portion was added an apyrase enzyme solution and an adenosine phosphate deaminase enzyme solution so that the mixture has the final enzyme concentration as shown in FIG. 4. Each of the sample solutions was subjected to reaction at 37° C. for 90 minutes to eliminate ATP in the yeast extract.

A 100 µl portion of the yeast extract from which free ATP had been eliminated (while the activities of both enzymes were maintained) was mixed with 100 µl of an ATP standard solution diluted to a concentration of $2\times10^{-11}$M with the ATP extracting reagent (KIKKOMAN), and the amount of luminescence A was measured quickly in the same manner as in Example 1.

In the same time, 100 µl of the yeast extract from which free ATP had been eliminated (while the activities of both enzymes were maintained) was mixed with 100 µl of the ATP extracting reagent (KIKKOMAN), and the amount of luminescence C was measured quickly in the same manner as in Example 1.

Also, 100 µl of the yeast extract from which free ATP had been eliminated (while the activities of both enzymes were maintained) was mixed with 100 µl of an ATP standard solution diluted to a concentration of $2\times10^{-11}$M with the ATP extracting reagent (KIKKOMAN), and maintained for 20 seconds before measurement. The amount of luminescence B was measured quickly in the same manner as in Example 1.

The percentage of the amount of luminescence of the ATP standard solution after 20 seconds (B–C) to the amount of luminescence of the initial ATP standard solution (A–C) was calculated and indicated as the rate of residual ATP.

Rate of residual ATP=$100\times$(B–C)/(A–C)

The result is illustrated in FIG. 4.

It is proved from the result in FIG. 4 that in the method for eliminating ATP with the combination of adenosine phosphate deaminase and apyrase, a high concentration of adenosine phosphate deaminase, that is the final concentration of 0.5–0.2 U/ml, leads to a low rate of residual ATP in the range of about 60% or less, while the final concentration of 0.1 U/ml or less causes little degradation of ATP and thus maintains the rate of residual ATP of 70% or more.

It is proved from the results in FIGS. 3 and 4 that if the final concentration of adenosine phosphate deaminase is too low, free ATP in the yeast extract is not eliminated insufficiently. As opposed to this, if the final concentration is too high, not only free ATP but also the extracted ATP (added ATP in this example) is decomposed and eliminated, so that the rate of residual ATP extracted may be undesirably lowered. However, if adenosine phosphate deaminase is added in an amount of 0.01–0.1 U/ml, free ATP is sufficiently eliminated, while the enzyme will scarcely affect the extracted ATP, and thus the rate of residual ATP can be maintained at a level of 70% or more.

EXAMPLE 4

Example for obtaining the optimal concentration of apyrase in the case of eliminating free ATP present in the yeast extract with the combination of adenosine phosphate deaminase and apyrase.

In the same manner as in Example 2, sterile yeast extract was prepared and divided into 8 of 5 ml portions, to which was added adenosine phosphate deaminase alone or the combination of the enzyme and apyrase, and the mixture was subjected to reaction at 37° C. for 90 minutes to eliminate free ATP in the yeast extract.

The luminescence of the yeast extract from which free ATP had been eliminated was measured to obtain the ATP concentration in the same manner as in Example 1.

Figure 5:
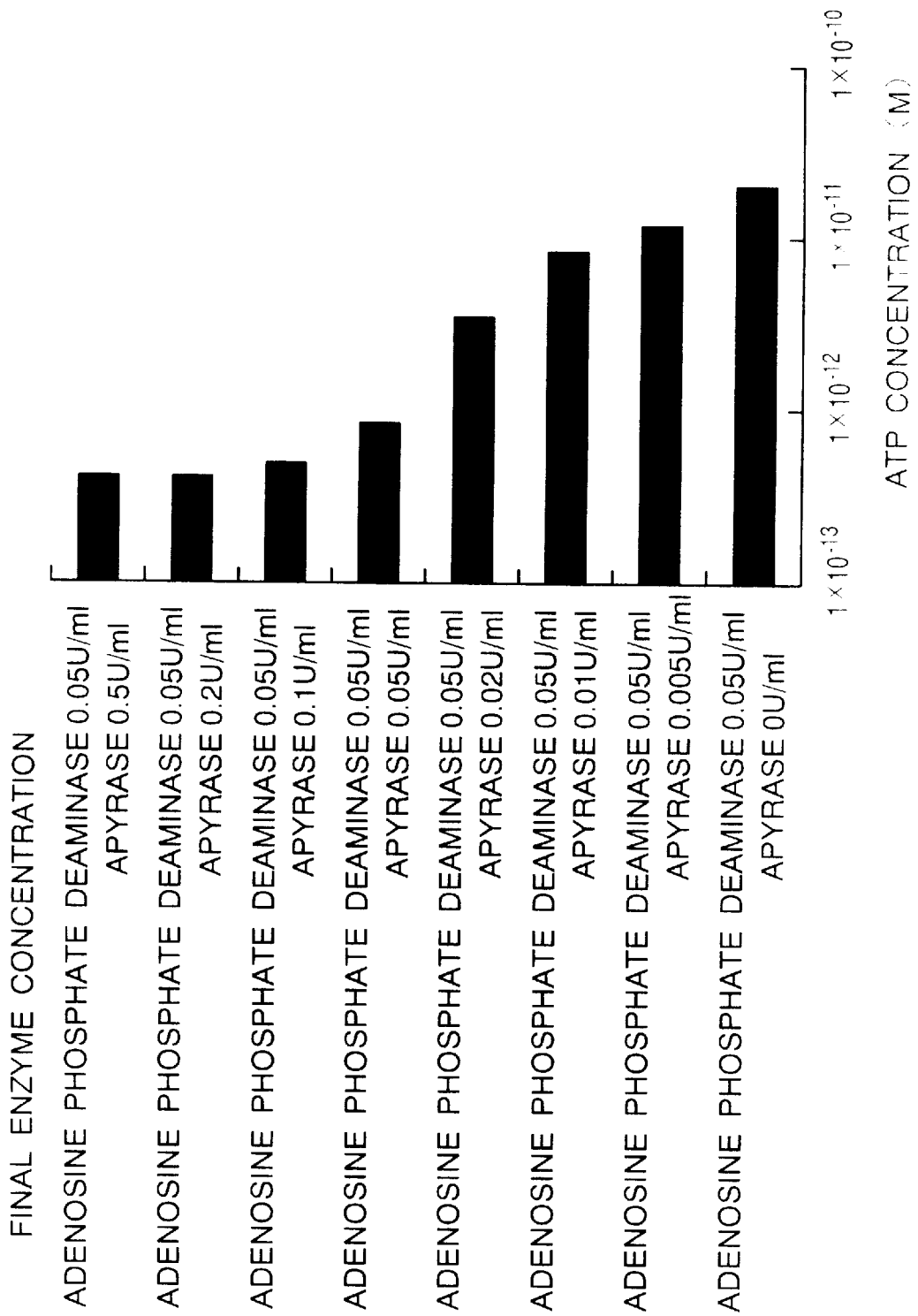
FIG. 5 illustrates the relationship between the activity of apyrase and the concentration of ATP remaining after the reaction in the method for eliminating ATP with adenosine phosphate deaminase in combination with apyrase.

The result is shown in FIG. 5.

It is proved from the result in FIG. 5 that in the portion to which adenosine phosphate deaminase alone was added, the ATP concentration can be reduced to a level of about $10^{-11}$M, while in the portion to which apyrase was further added as well as adenosine phosphate deaminase, the ATP concentration can be further reduced. In addition, as the final concentration of apyrase becomes higher, it is possible to reduce the ATP concentration. The final concentration of apyrase is preferably in the range of 0.01 U/ml or more, particularly 0.05–0.5 U/ml.

EXAMPLE 5

Example of measuring the rate of residual ATP by preliminarily eliminating free ATP in a yeast extract with the combination of adenosine phosphate deaminase and apyrase, then adding an ATP extracting agent containing a certain concentration of ATP and maintaining the mixture for a time required generally for the extraction of ATP, e.g. 20 seconds.

In the same manner as in Example 2, sterile yeast extract was prepared and divided into 8 of 5 ml portions, to which were added adenosine phosphate deaminase and apyrase, and the mixture was subjected to reaction at 37° C. for 90 minutes to eliminate free ATP in the yeast extract. The rate of residual ATP was measured with the reaction mixture thus obtained in the same manner as in Example 3.

Figure 6:
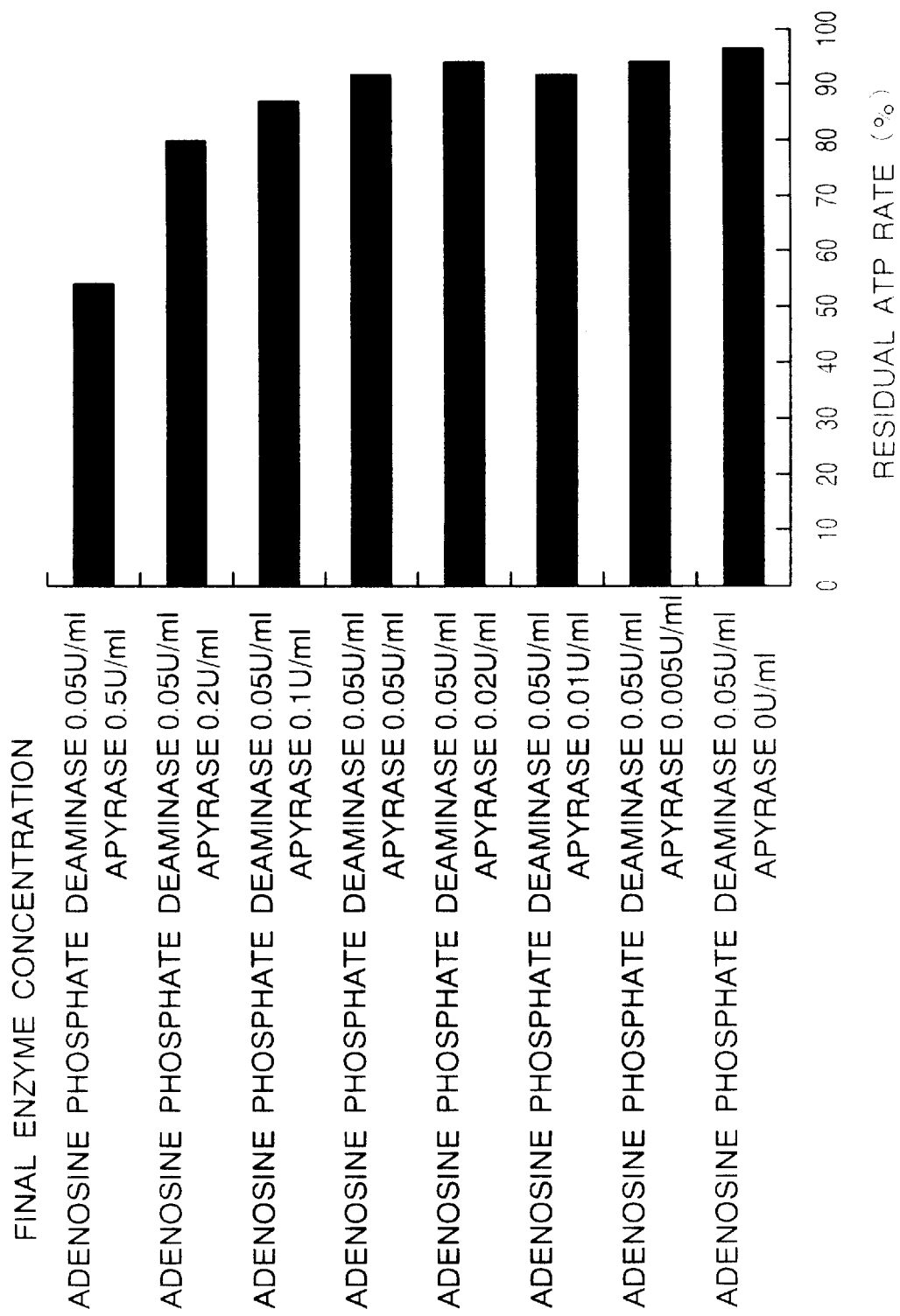
FIG. 6 illustrates the relationship between the activity of apyrase and the ratio of the remaining ATP in the method for eliminating ATP with adenosine phosphate deaminase in combination with apyrase.

The result is shown in FIG. 6.

It is proved from the result in FIG. 6 that in the method for eliminating ATP by using the combination of adenosine phosphate deaminase and apyrase, the rate of residual ATP remains in a low level of 60% or less in a high concentration of ATP, that is the final concentration of 0.5 U/ml, while the rate of residual ATP can be maintained at a high level of 70% or more since ATP is decomposed little in the final concentration of 0.2 U/ml or less.

It is also found from the results in FIGS. 5 and 6 that ATP is eliminated only insufficiently in the excessively low final concentration of apyrase, while the rate of residual ATP is lowered in the excessively high final concentration of apyrase. In contrast to this, when the final concentration of apyrase is in a level of 0.01–0.2 U/ml, the rate of residual ATP can be preferably maintained in a high level of 70% or more because of the satisfactory elimination of ATP.

EXAMPLE 6

Free ATP in a yeast extract is preliminarily eliminated with the combination of adenosine phosphate deaminase and apyrase, and then ATP extracting agents having varying concentratios of ATP is added in the presence of these enzymes. The mixture is maintained for times required generally for the extraction of ATP, i.e. 10, 20 and 30 seconds before measurement of the rate of residual ATP. The amounts of elimination of ATP in various concentrations extracted from biological cells by the decomposition of these enzymes in a certain extraction time can be estimated by this method.

In the same manner as in Example 2 was prepared a sterile yeast extract, to which were added an adenosine phosphate deaminase enzyme solution and an apyrase enzyme solution so as the final concentration of each of the enzyme solutions to be 0.05 U/ml, and the mixture was subjected to reaction at 30° C. to eliminate ATP in the yeast extract.

Figure 7:
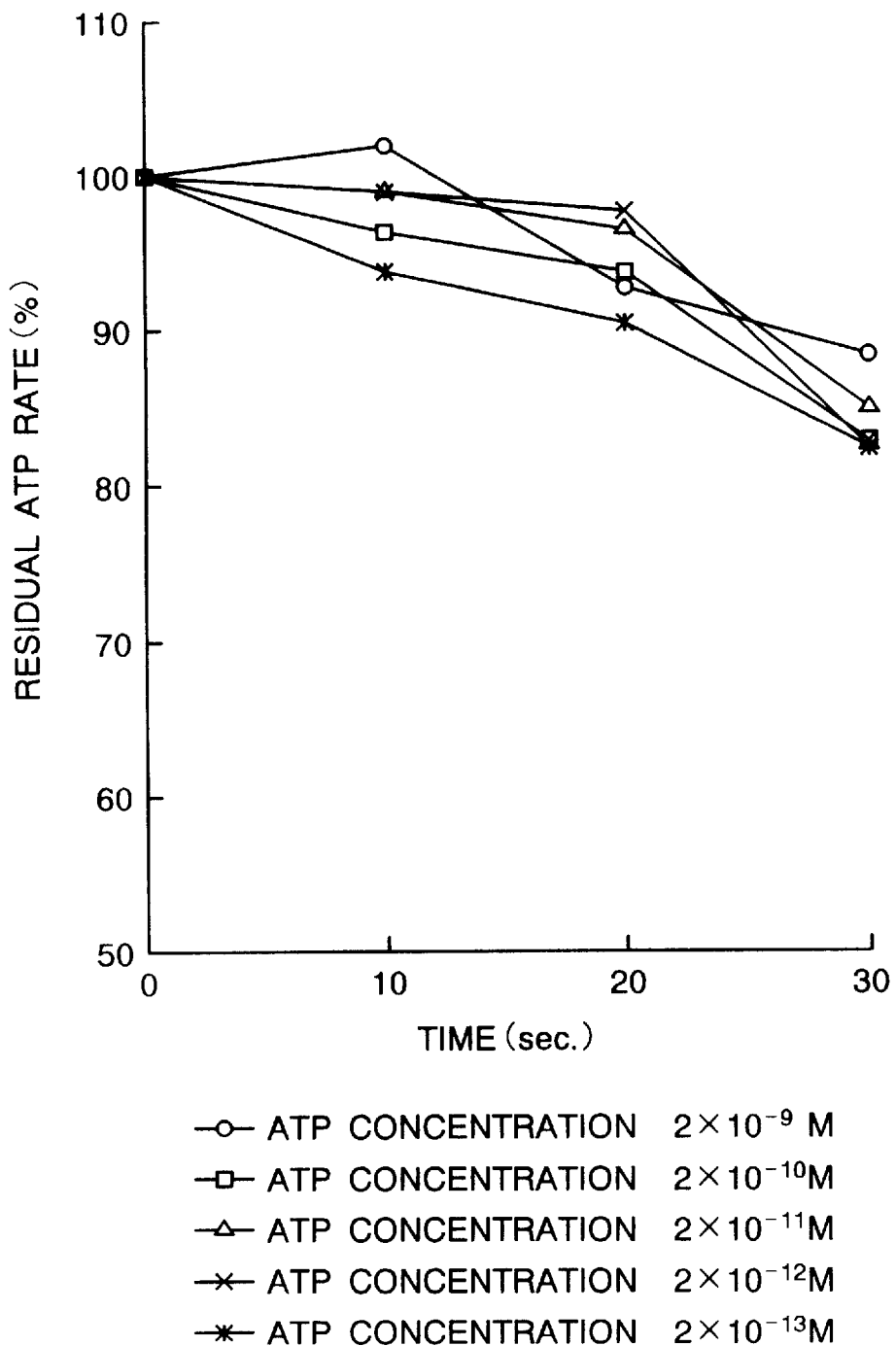
FIG. 7 illustrates the ratio of residual ATP with the passage of time in the reaction by the addition of various concentrations of standard ATP in the presence of adenosine phosphate deaminase in combination with apyrase.

To 100 μl of the yeast extract from which ATP had been eliminated was added 100 μl of the ATP standard solutions which had been diluted with the ATP extracting reagent (Kikko-Man) in various concentrations as shown in FIG. 7, and the luminescence of the mixture at 0 second and after standing 10, 20 and 30 seconds as shown in FIG. 7 was measured in the same manner as in Example 1 to obtain the rate of residual ATP.

The rate of residual ATP was measured according to the method described in Example 3.

The result is shown in FIG. 7.

It is revealed from the result in FIG. 7 that in the method for eliminating ATP with the combination of adenosine phosphate deaminase and apyrase, ATP is decreased almost in a constant and moderate rate without regard to the high ($2 \times 10^{-9}$M) or low ($2 \times 10^{-13}$M) ATP concentrations and still remains in a level of 80% or more after standing for 30 seconds.

That is to say, ATP added freshly will not be substantially decomposed by standing for 30 seconds which corresponds to the band of time for extracting ATP from microorganisms, and thus the extracted ATP (added ATP in this example) can be correctly determined.

It is thus possible to measure ATP extracted from microorganisms correctly and to count correctly the number of germ cells.

In addition, no difference is recognized between the residual rates in various ATP concentrations, so that the method has a feature of being affected nothing by the concentrations of biological cells, and thus the dilution operation of samples in the measurement of biological cells can be advantageously simplified.

EXAMPLE 7

Example for obtaining an optimal pH in the elimination of free ATP in a yeast extract by the addition of the combination of adenosine phosphate deaminase and apyrase to the yeast extract.

Figure 8:
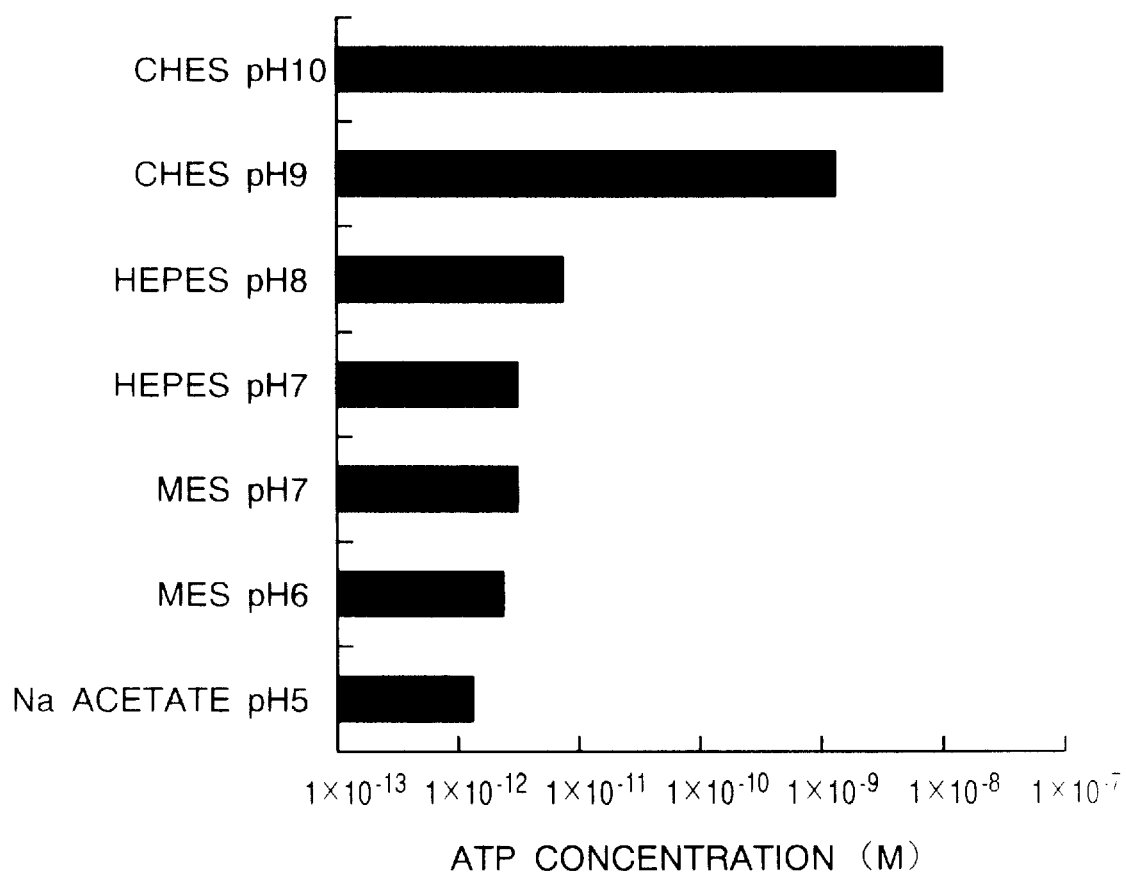
FIG. 8 illustrates the relationship between the pH in the enzyme reaction and the ratio of the residual ATP after the reaction in the method for eliminating ATP with adenosine phosphate deaminase in combination with apyrase.

Yeast extract powder (Difco) was added to 5 mM buffers having various pHs shown in FIG. 8 to give a 1% (w/v) solution, which was sterilized by filtration through a membrane filter to prepare a sterile yeast extract having a pH shown in FIG. 8.

The yeast extract was divided into 7 of 5 ml portions, to which were added adenosine phosphate deaminase and apyrase so that the final concentrations become 0.05 U/ml, and the mixture was subjected to reaction at 37° C. for 30 minutes before measurement of luminescence of the yeast extract thus obtained following to the procedure described below.

Luminescence was measured in the same manner as in Example 1 to determine the ATP concentration.

The result is shown in FIG. 8.

It is revealed from the result in FIG. 8 that in the case of eliminating free ATP present in the yeast extract with the combination of adenosine phosphate deaminase and apyrase, pH is preferably in the range of 5.0–8.0, particularly 5.0–7.0.

EXAMPLE 8

Example for obtaining the optimal temperature in the case of eliminating free ATP in yeast extract with the combination of adenosine phosphate deaminase and apyrase.

Figure 9:
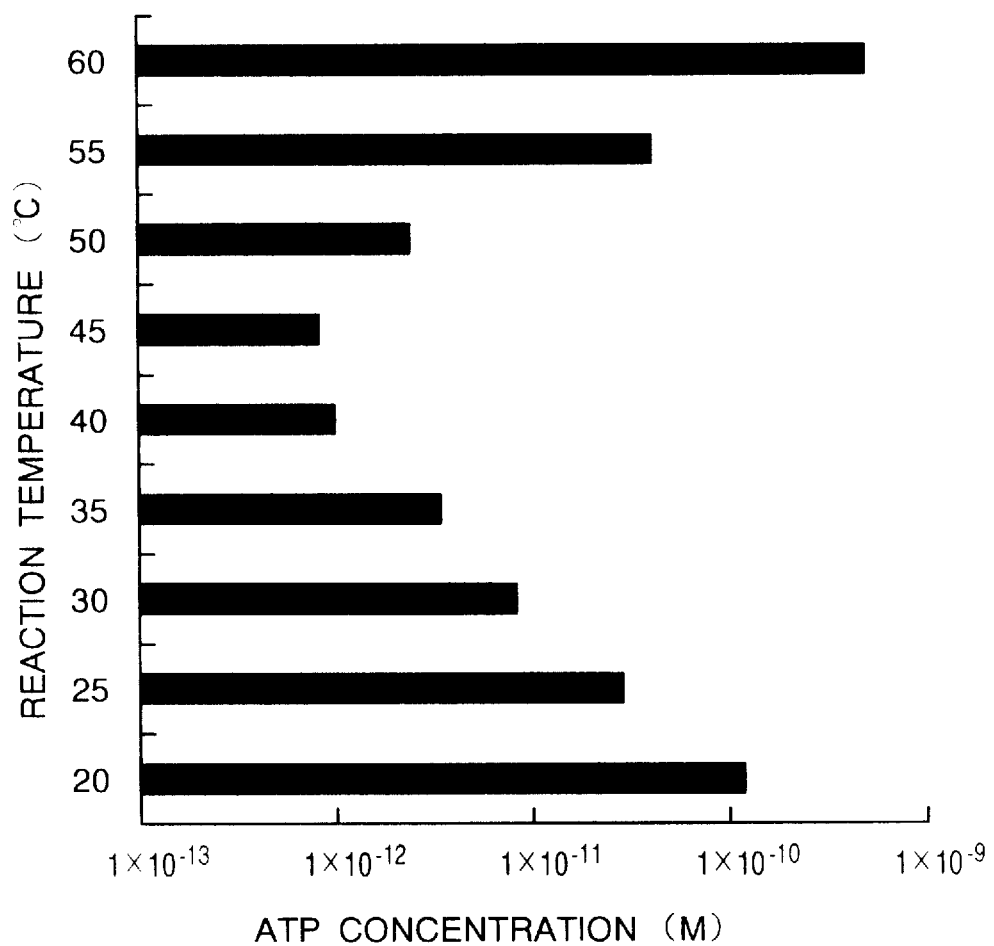
FIG. 9 illustrates the relationship between the temperatures in the enzymatic reaction and the ratio of the residual ATP after the reaction in the method for eliminating ATP with adenosine phosphate deaminase in combination with apyrase.

In the same manner as in Example 2 was prepared a sterile yeast extract, which was divided into 9 of 5 ml portions, to which were added adenosine phosphate deaminase and apyrase so as the final concentration of each of the enzyme solutions to be 0.05 U/ml, and the mixture was subjected to reaction at a temperature described in FIG. 9 for 30 minutes. The samples thus obtained were subjected to the measurement of luminescence by the following method.

Luminescence was measured in the same manner as in Example 1 to obtain ATP concentration.

The result is shown in FIG. 9.

It is revealed from the result in FIG. 9 that free ATP present in the yeast extract is eliminated with the combination of adenosine phosphate deaminase and apyrase preferably at a temperature in the range of 25°–55° C., more preferably 35°–50° C., most preferably 40°–45° C.

The calibration curve of ATP employed in following Examples of the present invention was next prepared with a luminometer LUMITESTER K-100 (KIKKOMAN).

That is to say, 100 μl of super pure water was added to 100 μl of an ATP standard solution having a certain concentration, followed by 100 μl of a luciferin-luciferase luminescent reagent, and the ralative amount of luminescence S was measured with a luminometer LUMITESTER K-100 (KIKKOMAN).

At the same time, 100 μl of the luminescent reagent was added to 200 μl of super pure water, and the luminescence was measured in the same manner as above to obtain the amount of luminescence in the luminescent reagent R (blank).

Figure 10:
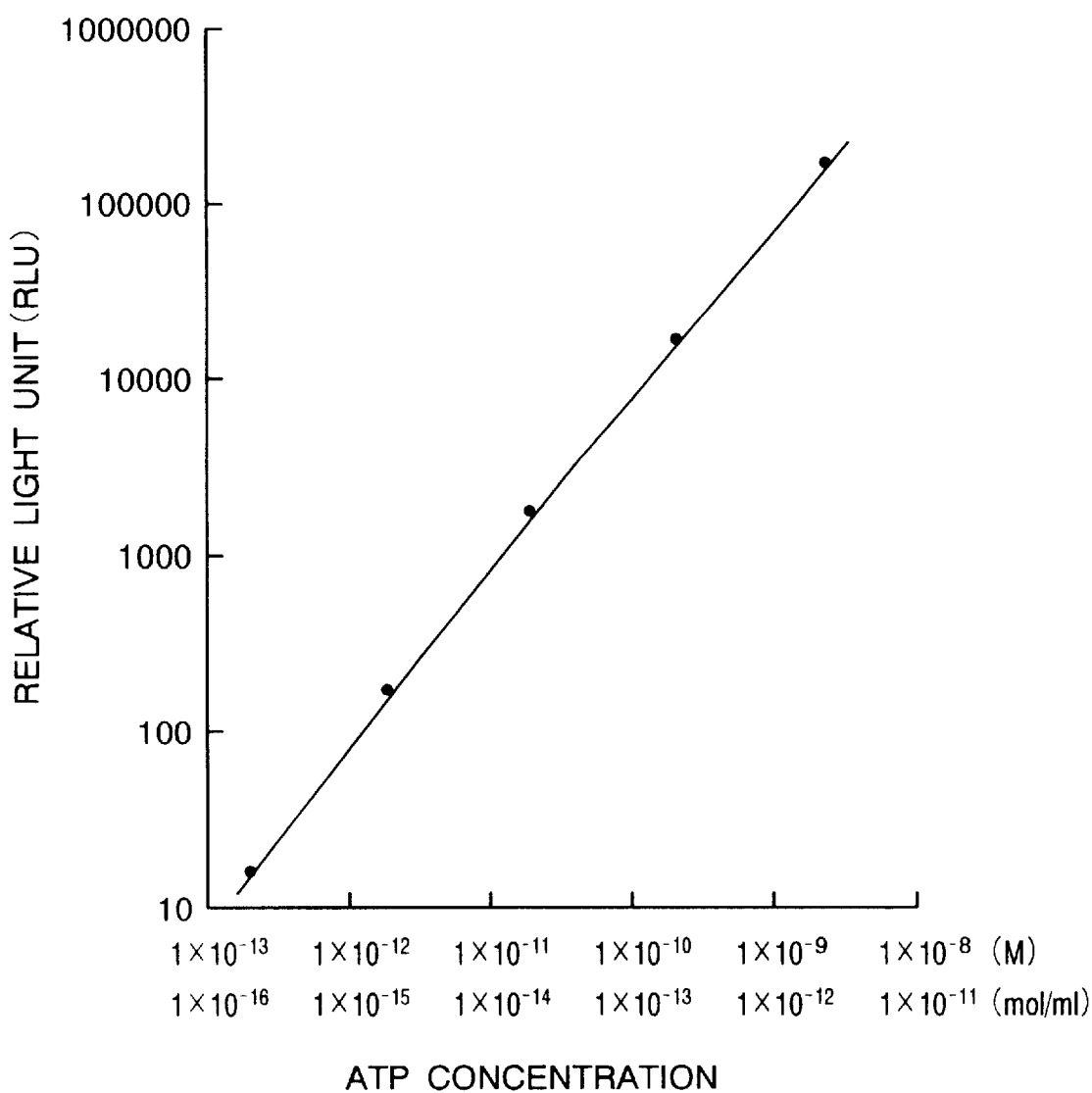
FIG. 10 illustrates the calibration curve of ATP with a luminometer "Lumitester-K-100" manufactured by Kikkoman.

The net amount of luminescence Z of ATP was obtained from the difference S−R, so that the calibration curve shown in FIG. 10 was prepared with the net amount of luminescence Z as the Y axis and the ATP concentration as the X axis of the coordinates.

EXAMPLE 9

Example of measuring the amount of ATP per CFU in *Staphylococcus aureus* under the condition that the effect of the ATP eliminator has been removed.

The following steps were carried out in this sequence to count the number of biological cells in the culture medium of *Staphylococcus aureus* as a practical subject microorganism:

step 1: culturing the subject microorganism in a standard liquid medium to prepare the culture solution;
step 2: elimination of free ATP from the culture solution;
step 3: preparation of a dilution with a standard liquid medium;
step 4: preparation of a suspension of the subject microorganism by diluting the culture solution from which free ATP had been eliminated;
step 5: measurement of luminescence of free ATP in the suspension of the subject microorganism;

step 6: addition of an ATP extracting agent to the subject microorganism and measurement of luminescence of the total ATP consisting of free ATP which is present before addition of the extracting agent and the extracted ATP (ATP in the cells);

step 7: calculation of the amount of luminescence of ATP in the cells;

step 8: calculation of the corrected amount of luminescence of ATP in the cells;

step 9: calculation of the concentration of ATP on the basis of the corrected amount;

step 10: calculation of CFU per ml of the suspension of the subject microorganism by the pour culture method;

step 11: measurement of the amount of ATP per CFU.

(Step 1: Culturing the subject microorganism in a standard liquid medium to prepare the culture solution)

In 8 ml of a standard liquid medium (0.25% yeast extract, 0.5% triptone, 0.1% glucose, pH 7.1) was inoculated *Staphylococcus aureus* ATCC 25923 in one platinum loop amount and stationary cultured at 35° C. overnight to obtain a culture solution of the microorganism.

(Step 2: Elimination of free ATP from the culture solution)

To 2 ml of the culture solution (containing a large amount of viable cells) were added apyrase and adenosine phosphate deaminase so that the final concentrations are 0.05 U/ml, respectively, and the mixture was treated at 35° C. for 30 minutes in order to eliminate preliminarily free ATP in the culture solution.

The blank level of ATP can be lowered by the treatment.

(Step 3: Preparation of a dilution with a standard liquid medium)

At the same time, apyrase and adenosine phosphate deaminase were added to 100 ml of the standard liquid medium having inoculated therein no microorganism described above so that the final concentrations are 0.05 U/ml, respectively, and the mixture was reacted at 35° C. for 90 minutes, then sterilized in an autoclave at 120° C. for 15 minutes to deactivate the enzymes and to prepare a dilution comprising a sterile standard liquid medium from which free ATP had been eliminated.

(Step 4: Preparation of a suspension of the subject microorganism by diluting the culture solution from which free ATP had been eliminated)

The culture solution prepared in step 2 was diluted with the dilution obtained in step 3 to prepare the 10,000 time dilution of the microorganism suspension.

The dilution was left standing 35° C. for 30 minutes before use as the sample for measuring luminescence.

(Step 5: Measurement of luminescence of free ATP in the suspension of the subject microorganism)

To 100 μl of the 10,000 time dilution of the microorganism suspension was added 100 μl of super pure water, followed by 100 μl of the luminescent reagent, and the mixture was subjected to the measurement of luminescence with LUMITESTER K-100 (KIKKOMAN) in order to determine the amount of luminescence of free ATP (referred to hereinafter as free luminescence amount F) in the dilution of the microorganism suspension (Step 6: Addition of an ATP extracting agent to the subject microorganism and measurement of luminescence of the total ATP consisting of free ATP which is present before addition of the extracting agent and the extracted ATP (ATP in the cells))

To 100 μl of the dilution of the microorganism suspension was added 100 μl of the ATP extracting reagent (KIKKOMAN), followed by 100 μl of the luminescent reagent after 20 seconds at room temperature, and the mixture was subjected to the measurement of luminescence with LUMITESTER K-100 (KIKKOMAN) in order to determine the amount of luminescence of the total ATP (T) of the free ATP and ATP extracted from the microorganism cells by the action of the extracting agent.

(Step 7: Calculation of the amount of luminescence of ATP in the cells)

The amount of luminescence of ATP in the cells can be determined correctly by subtracting the free luminescence amount (F) from the total amount of luminescence (T).

(Step 8: Calculation of the corrected amount of luminescence of ATP in the cells)

The bioluminescence reaction described above of luciferin-luciferase is inhibited somewhat by ingredients contained in a sample, and must be corrected in order to determine the amount of luminescence without luminescence inhibition. The amount of luminescence was corrected as follows.

That is, 100 μl of $2 \times 10^{-10}$M ATP standard solution was added to 100 μl of the subject microorganism suspension, followed by 100 μl of the luminescent reagent after 20 seconds, and the amount of luminescence was measured with LUMITESTER K-100 (KIKKOMAN) to determine the amount of internal standard luminescence H.

The amount of luminescence was measured to determine the amount of true standard luminescence G in the same manner as in the method for determining the above described amount of internal standard luminescence except that 100 μl of sterile super pure water was used in place of 100 μl of the subject microorganism suspension.

Then, luminescence Y (corrected value) of intracellular ATP in case of having no luminescence inhibition was determined from the following calculation formula:

$$Y=(T-F)/K,$$

$$K=(H-F)/G$$

herein H: internal standard luminescence amount

F: free luminescence amount

G: true standard luminescence amount

K: rate of luminescence

T−F: luminescence amount of intracellular ATP obtained in the previous step

T: total luminescence amount.

(Step 9: Calculation of the concentration of ATP on the basis of the corrected amount)

The concentration of ATP corresponding to the (corrected) amount of luminescence of ATP in the cells in the absence of luminescence inhibition was determined according to the calibration curve shown in FIG. 10 which had been prepared preliminarily.

(Step 10: Calculation of CFU per ml of the suspension of the subject microorganism by the pour culture method)

A certain amount of the subject microorganism suspension diluted appropriately was added to a sterile plate with a sterile pipette under the sterile condition, followed by the solution of a standard agar medium (0.25% yeast extract, 0.5% triptone, 0.1% glucose, pH 7.1, 2.0% agar) cooled to 50° C., and the plate was capped, moved and rotated slowly in the horizontal directions to mix the subject microorganism suspension with the medium homogeneously, cultured at 35° C. for 24 hours. The appearing colonies were counted to estimate the number of microorganisms per ml of the original solution (Colony Forming Unit: CFU) in consideration of the dilutions.

(Step 11: Measurement of the amount of ATP per CFU)

The amount of ATP per CFU of *Staphylococcus aureus* was determined by dividing the concentration of ATP (mole/ml) corresponding to the (corrected) amount of luminescence of ATP in the cells in the absence of luminescence inhibition by CFU per ml of the subejct microorganism suspension obtained in step 10 (CFU/ml).

As a result, the amount of ATP of $2\times10^{-17}$ mole/CFU was obtained.

The results described above are shown in Table 1.

| The amount of ATP per CFU of *Staphylococcus aureus* (mole/CFU) | |
|---|---|
| Dilution | 10,000 times |
| Total luminescence (T) | 16,198 |
| Free luminescence (F) | 905 |
| T − F luminescence | 15,293 |
| Corrected luminescence | 21,268 |
| ATP concentration (mole/ml) | $2.54 \times 10^{-13}$ |
| Experimental value (pour culture method) (CFU/ml) | $1.27 \times 10^{4}$ |
| Amount of ATP (mole/CFU) | $2.00 \times 10^{-17}$ |

EXAMPLE 10

Method for measuring the CFU in the viable cells in the diluted suspension of the *Staphylococcus aureus* of which activity was maintained with the measurement of ATP per CFU (ca. $2\times10^{-17}$) in *Staphylococcus aureus* obtained in Example 9 under the influence of the ATP eliminator.

Step 1: Dilution of the culture solution to a certain concentraion to prepare the diluted suspension of the subject microorganism;

Step 2: Elimination of free ATP from the diluted suspension of the subject microorganism;

Step 3: Measurement of luminescence of free ATP in the diluted suspension of the subject microorganism;

Step 4: Addition of an ATP extracting agent to the subject microorganism and measurement of luminescence of the total ATP consisting of free ATP present in a trace amount and the extracted ATP (ATP in the cells);

Step 5: Calculation of the amount of luminescence of ATP in the cells;

Step 6: Calculation of the corrected amount of luminescence;

Step 7: Calculation of the concentration of ATP on the basis of the corrected amount;

Step 8: Calculation of CFU per ml of the diluted suspension of *Staphylococcus aureus*;

Step 9: Comparative example (calculation of CFU per ml of the diluted suspension of the subject microorganism by the pour culture method).

(Step 1: Dilution of the culture solution to a certain concentraion to prepare the diluted suspension of the subject microorganism)

The culture solution of *Staphylococcus aureus* obtained in step 1 of the preceding example was diluted to 10,000, 100,000, 1,000,000 and 10,000,000 times with a standard liquid medium sterilized by heating in an autoclave (diluent) to obtain the diluted suspensions of the subject microorganism.

(Step 2: Elimination of free ATP from the diluted suspension of the subject microorganism)

Apyrase and adenosine phosphate deaminase were added to the above described diluted suspensions of the subject microorganism so as the final concentrations of these enzymes to be 0.05 U/ml, and the mixture was reacted at 35° C. for 30 minutes to eliminate ATP.

(Step 3; Measurement of luminescence of free ATP in the diluted suspension of the subject microorganism)

To 100 μl of the diluted suspension of the subject microorganism was added 100 μl of super pure water, followed by 100 μl of the luminescent reagent, and the mixture was subjected to the measurement of luminescence with LUMITESTER K-100 (KIKKOMAN) in order to determine the amount of luminescence. The amount of luminescence of the free ATP in the suspension of the subject microorganism (F) can be determined by this measurement.

(Step 4: Addition of an ATP extracting agent to the subject microorganism and measurement of luminescence of the total ATP consisting of free ATP present in a trace amount and the extracted ATP (ATP in the cells))

To 100 μl of the diluted suspension of the subject microorganism was added 100 μl of the ATP extracting reagent (KIKKOMAN), followed by 100 μl of the luminescent reagent after 20 seconds at room temperature, and the mixture was subjected to the measurement of luminescence with LUMITESTER K-100 (KIKKOMAN) in order to determine the amount of luminescence. The sum of the luminescences of ATP in the cells extracted by the action of the extracting agent and of the free ATP can be determined by this measurement and thus was regarded as the total amount of luminescence T.

(Step 5: Calculation of the amount of luminescence of ATP in the cells)

The amount of luminescence of ATP in the cells is determined correctly by subtracting the free luminescence amount (F) from the total amount of luminescence (T).

(Step 6: Calculation of the corrected amount of luminescence)

In each of the previous steps described above, the bioluminescence reaction of luciferin-luciferase is inhibited somewhat by ingredients contained in the suspension, and thus corrected by the following method in order to determine the amount of luminescence without luminescence inhibition.

A 100 μl portion of $2\times10^{-10}$M ATP standard solution was added to 100 μl of the diluted suspension of the subject microorganism, followed by 100 μl of the luminescent reagent after 20 seconds, and the amount of internal standard luminescence H was determined with LUMITESTER K-100 (KIKKOMAN).

The amount of true standard luminescence G was determined in the same manner as in the method for determining the above described amount of internal standard luminescence H except that 100 μl of sterile super pure water was used in place of 100 μl of the diluted suspension of the subject microorganism.

Then, luminescence Y (corrected value) of intracellular ATP in case of having no luminescence inhibition was determined from the following calculation formula:

$Y=(T-F)/K$, $K=(H-F)/G$ herein H: internal standard luminescence amount

F: free luminescence amount

G: true standard luminescence amount

K: rate of luminescence

T−F: luminescence amount of intracellular ATP obtained in the previous step

T: total luminescence amount.

(Step 7: Calculation of the concentration of ATP corresponding to the corrected amount of luminescence)

The concentration of ATP corresponding to the corrected amount of luminescence Y was determined according to the calibration curve shown in FIG. 10 which had been prepared preliminarily.

(Step 8: Calculation of the concentration of CFU per ml of the diluted suspension of Staphylococcus aureus)

The ATP concentration (mole/ml) corresponding to the corrected amount of luminescence obtained in step 7 was divided by the amount of ATP (ca. $2 \times 10^{-17}$ mole) per CFU of Staphylococcus aureus obtained in step 11 (final step) in Example 9 to calculate the CFU concentration per ml of the diluted suspension of Staphylococcus aureus.

(Step 9: Comparative Example (Calculation of CFU per ml of the diluted suspension of the subject microorganism by the pour culture method)

A certain amount of the appropriately diluted suspension of the subject microorganism was added to a sterile plate with a sterile pipette under the sterile condition, followed by the solution of a standard agar medium cooled to 50° C., and the plate was capped, moved and rotated slowly in the horizontal directions to mix the subejct microorganism suspension with the medium homogeneously, cultured at 35° C. for 24 hours. The appearing colonies were counted to estimate the number of microorganisms per ml of the subject microorganism suspension (CFU) in consideration of the dilutions.

The CFU concentration thus obtained was regarded as the observed value (CFU/ml).

The results described above are shown in Table 2.

The measurement of viable germ concentration of Staphylococcus aureus (CFU/ml)

| Dilution (times) | 10,000 | 100,000 | 1,000,000 | 10,000,000 |
|---|---|---|---|---|
| Total luminescence (T) | 10,520 | 1,212 | 125 | 23 |
| Free luminescence (F) | 27 | 18 | 12 | 13 |
| T − F luminescence | 10,493 | 1,194 | 113 | 10 |
| Corrected luminescence | 22,493 | 2,558 | 243 | 23 |
| ATP concentration (mole/ml) | $2.68 \times 10^{-13}$ | $3.05 \times 10^{-14}$ | $2.90 \times 10^{-15}$ | $2.68 \times 10^{-16}$ |
| Calculated value (present invention) (CFU/ml) | $1.34 \times 10^4$ | $1.53 \times 10^3$ | $1.45 \times 10^2$ | $1.34 \times 10$ |
| Observed value (pour culture method) (CFU./ml) | $1.11 \times 10^4$ | $1.34 \times 10^3$ | $1.07 \times 10^2$ | $1.00 \times 10$ |

EXAMPLE 11

(Method for measuring the amount of ATP per CFU of Escherichia coli (mole/CFU))

The amount of ATP per CFU was measured in the same manner as the method for measuring the amount of ATP per Staphylococcus aureus in Example 9 except that Staphylococcus aureus ATCC 25923 was replaced by Escherichia coli NISL B-4300.

The results are shown in Table 3.

The amount of ATP per CFU of Escherichia coli (mole/CFU)

| Dilution | 10,000 times |
|---|---|
| Total luminescence (T) | 10,495 |
| Free luminescence (F) | 948 |
| T − F luminescence | 9,547 |
| Corrected luminescence | 13,277 |
| ATP concentration (mole/ml) | $1.58 \times 10^{-13}$ |
| Experimental value (pour culture method) (CFU/ml) | $3.58 \times 10^4$ |
| Amount of ATP (mole/CFU) | $4.42 \times 10^{-18}$ |

EXAMPLE 12

(Measurement of viable cells in the diluted culture suspension of Escherichia coli (CFU/ml))

The concentration of viable cells (CFU/ml) in the diluted culture suspension of Escherichia coli was measured in the same manner as the method for measuring the amount of the viable cells of Staphylococcus aureus in Example 10 except that Staphylococcus aureus ATCC 25923 was replaced by Escherichia coli NISL B-4300.

The results are shown in Table 4.

The measurement of viable germ concentration of Escherichia coli (CFU/ml)

| Dilution (times) | 10,000 | 100,000 | 1,000,000 | 10,000,000 |
|---|---|---|---|---|
| Total luminescence (T) | 7,553 | 902 | 138 | 29 |
| Free luminescence (F) | 45 | 31 | 18 | 18 |
| T-F luminescence | 7,508 | 871 | 120 | 11 |
| Corrected luminescence | 16,168 | 1,874 | 258 | 24 |
| ATP concentration (mole/ml) | $1.93 \times 10^{-13}$ | $2.23 \times 10^{-14}$ | $3.08 \times 10^{-15}$ | $2.82 \times 10^{-16}$ |
| Calculated value (present invention) (CFU/ml) | $4.37 \times 10^4$ | $5.05 \times 10^3$ | $6.97 \times 10^2$ | $6.38 \times 10$ |
| Observed value (pour culture method) (CFU./ml) | $4.86 \times 10^4$ | $4.80 \times 10^3$ | $4.29 \times 10^2$ | $4.20 \times 10$ |

EXAMPLE 13

(Method for measuring the amount of ATP per CFU of Saccharomyces cerevisiae (mole/CFU))

The amount of ATP per viable cell (CFU) of Saccharomyces cerevisiae (mole/CFU) was measured in the same manner as the method for measuring the amount of ATP per CFU of Staphylococcus aureus in Example 9 except that as the medium, a "YM medium (1% glucose, 0.5% peptone, 0.3% yeast extract, 0.3% malt extract, pH 6.0)" was used in place of the "standard liquid medium", and a "YM medium containing agar (1% glucose, 0.5% peptone, 0.3% yeast extract, 0.3% malt extract, 2% agar, pH 6.0)" was used in place of the "standard agar medium", and as subject microorganism, "Saccharomyces cerevisiae NISL Y-3398" was used in place of "Staphylococcus aureus ATCC 25923".

The results are shown in Table 5.

TABLE 5

| The amount of ATP per CFU of Saccharomyces cerevisiae (mole/CFU) | |
|---|---|
| Dilution | 10,000 times |
| Total luminescence (T) | 20,015 |
| Free luminescence (F) | 1,119 |
| T − F luminescence | 18,896 |
| Corrected luminescence | 29,894 |
| ATP concentration (mole/ml) | $3.56 \times 10^{-13}$ |
| Experimental value (pour culture method) (CFU/ml) | $2.95 \times 10^3$ |
| Amount of ATP (mole/CFU) | $1.21 \times 10^{-16}$ |

EXAMPLE 14
(Measurement of viable cells in the diluted culture suspension of *Saccharomyces cerevisiae* (CFU/ml))

The concentration of viable cells (CFU/ml) in the diluted culture suspension of *Saccharomyces cerevisiae* was measured in the same manner as the method for measuring the amount of the viable cells of *Staphylococcus aureus* in Example 10 except that *Staphylococcus aureus* ATCC 25923 was replaced by *Saccharomyces cerevisiae* NISL Y-3398.

The results are shown in Table 6.

TABLE 6

| The measurement of viable germ concentration of Saccharomyces cerevisiae (CFU/ml) | | | |
|---|---|---|---|
| Dilution (times) | 10,000 | 100,000 | 1,000,000 |
| Total luminescence (T) | 15,871 | 1,522 | 184 |
| Free luminescence (F) | 17 | 11 | 10 |
| T − F luminescence | 15,854 | 1,511 | 174 |
| Corrected luminescence | 36,032 | 3,434 | 395 |
| ATP concentration (mole/ml) | $4.30 \times 10^{-13}$ | $4.09 \times 10^{-14}$ | $4.71 \times 10^{-15}$ |
| Calculated value (present invention) (CFU/ml) | $3.55 \times 10^3$ | $3.38 \times 10^2$ | $3.89 \times 10$ |
| Observed value (pour culture method) (CFU./ml) | $4.05 \times 10^3$ | $3.35 \times 10^2$ | $3.40 \times 10$ |

It is proved from the results of Table 1–6 that a method for measuring ATP equivalent to the pour culture method which has been conventionally regarded to have high precision and high reliability can be provided according to the process of the present invention. According to the present invention, it is also possible to eliminate a culture step required for the conventional method and to finish the test cycle in several ten minutes, so that the time required for the treatment can be extensively shortened as compared with the conventional method. In addition, it is possible to exclude equipments for dilution and to save time and labor for dilution and preparing a medium.

Furthermore, in the standard liquid medium and the YM medium, free ATP exhibited the relative light unit (RLU) of 92100 and 139350, respectively, and thus the number of cells could not be measured.

However, when ATP per CFU was in a relatively large amount like the case of *Staphylococcus aureus* or *Saccharomyces cerevisiae* due to the decline of free luminescence by eliminating free ATP with the ATP eliminating reagent, it was possible to detect germ at a minimum concentration of several ten CFU/ml. When ATP per CFU was in a relatively low level like the case of *Escherichia coli*, it was possible to detect germ at a minimum concentration of 40–50 CFU/ml. Thus, the present invention has a satisfactorily high detection sensitivity even if the ATP eliminating reagent maintains the activity.

In this connection, it is revealed that when the correlation coefficient between the calculated number of cells obtained by the process of the present invention (CFU/ml) and the observed number of cells obtained by the pour culture method was determined, it was 0.99 in either of the bacteria and showed an extremely high correlation, and the number of cells can be measured correctly if the ATP eliminating reagent maintains the activity.

Figure 11:
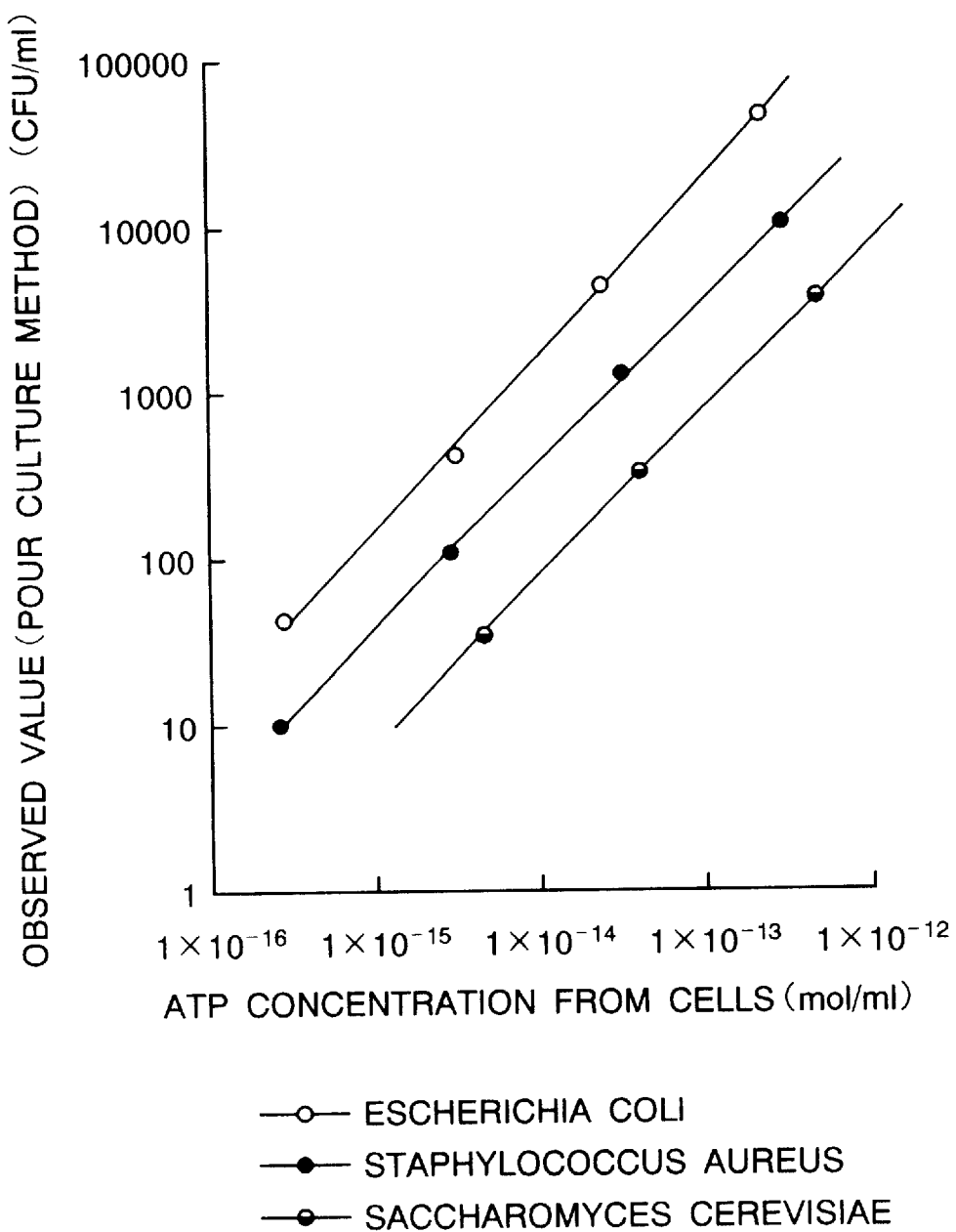
FIG. 11 illustrates the relationship between the concentrations of ATP derived from microorganisms according to the present invention and the number of cells obtained by the pour culture method.

The relationship between the concentration of ATP (mole/ml) extracted from each of the microorganisms which is determined by the present invention and the observed number of cells (CFU/ml) which is determined by the pour culture method is shown in FIG. 11.

A calibration curve having good linearity in either of the microorganisms can be obtained from this relationship.

It is thus revealed that the number of cells can be measured correctly from the concentration (mole/ml) of ATP extracted from microorganisms.

EXAMPLE 15
(Method for eliminating free ATP in the liquid nutrient medium, SCD medium)

Adenosine phosphate deaminase was added to the liquid nutrient medium, SCD medium so that the final concentration of the enzyme was 0.01 U/ml, and the mixture was maintained at 35° C. for 120 minutes. Samples were taken out with the passage of time to measure luminescence.

To 100 μl of the sample was added 100 μl of 0.3 mM phosphate buffer (pH 7.2), followed by 100 μl of LUCIFER LU (ATP measuring reagent, KIKKOMAN), and the amount of luminescence was measured with a LUMITESTER K-100 (KIKKOMAN).

The result is shown in Table 7.

It has been revealed from the result of Table 7 that the initial ATP concentration in the SCD medium (that is, the ATP concentration in the absence of the effect of adenosine phosphate deaminase) exhibits the relative luminescent unit of 2718, but is substantially eliminated in 60 minutes as the free ATP is rapidly descreased with the initiation of the action of the enzyme.

TABLE 7

| Treatment time (min) | Relative light unit (RLU) |
|---|---|
| 0 | 2718 |
| 30 | 41 |
| 60 | 11 |
| 120 | 7 |

EXAMPLE 16
(Method for quantitatively determining *Bacillus subtilis* in soya koji contaminated therewith)

Figure 12:
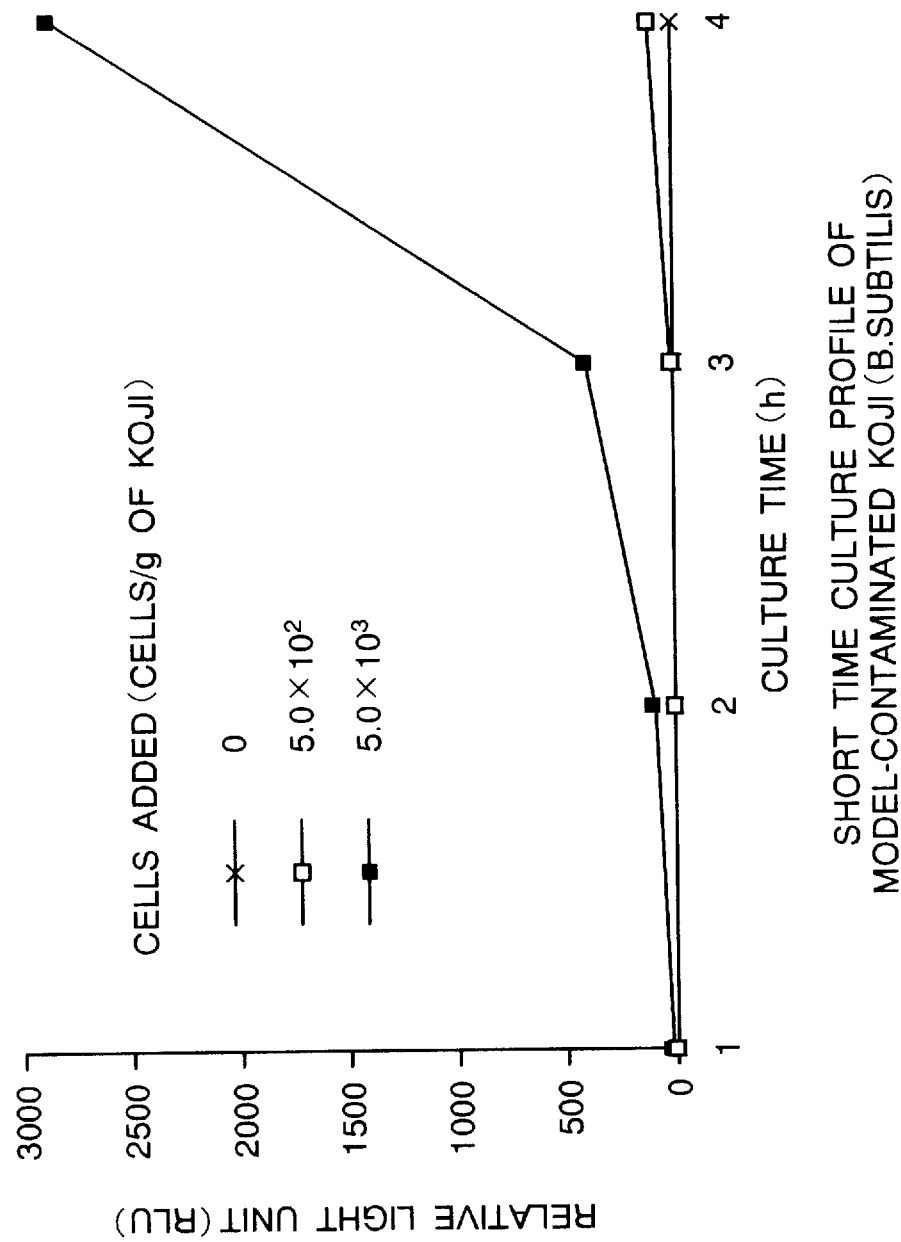
FIG. 12 illustrates the result of the quantitative determination of Bacillus subtilis in koji for soy sauce contaminated with B. subtilis.

To 20 g of substantially sterile soya koji was added *Bacillus subtilis* AHU1035 in an amount (counts/g of koji) as shown in FIG. 12 to obtain soya koji contaminated artificially with *Bacillus subtilis*.

To the soya koji was added 80 ml of 0.3 mM phosphate buffer (pH 7.2), and the mixture was sufficiently stirred to prepare a suspension.

Next, to 8 ml of the suspension were added 2 ml of the SCD medium preparation described in the above described Example 15 and having a 4 times concentration (6.0% triptone, 2.0% soytone, 2.0% NaCl, pH 7.3), 50 μl of a 70% ethanolic solution of 2% NYSTATIN (growth inhibitor of koji), and 20 μl (final concentration 0.01 U/ml) of adenosine phosphate deaminase (5 U/ml), and only *Bacillus subtilis* was stationally cultured selectively at 35° C. During culturing, the culture solutions were taken out in an amount of 100 μl with the passage of time, and 100 μl of the ATP extracting reagent (KIKKOMAN) was added to the solution, followed by 100 μl of LUCIFER LU (ATP measuring reagent, KIKKOMAN) after 20 seconds in order to measure luminescence with a LUMITESTER K-100 (KIKKOMAN) (the measured value being represented by relative light unit).

The relative proliferation of *Bacillus subtilis* with the passage of time can be examined by measuring the amount of luminescence.

The results are shown in FIG. 12.

As described above, it has been revealed from the result of Table 7 that free ATP is present in a high concentration and exhibits a relative light unit of 2718 in the SCD medium. This value cannot be distinguished from the value of the ATP concentration (relative light unit=ca. 3000) from *Bacillus subtilis* in the portion of $5.0 \times 10^3$/g of koji in this example after 4 hours. It is impossible to perform the correct measurement of *Bacillus subtilis* by the conventional method in which free ATP in the SCD medium is not eliminated.

In contrast, as apparent from the result in FIG. 12, it is possible to measure correctly the amount of ATP from *Bacillus subtilis* by eliminating preliminarily the free ATP in the SCD medium according to the present invention.

EXAMPLE 17
(Method for quantitatively determining lactic acid bacteria in soya koji contaminated therewith)

The quantitative determination of lactic acid bacteria in soya koji contaminated therewith was carried out in the same manner as the method for quantitatively determining *Bacillus subtilis* in soya koji contaminated therewith except that *Bacillus subtilis* was replaced by lactic acid bacteria *Leuconostoc mesenteroides* AHU1065.

Figure 13:
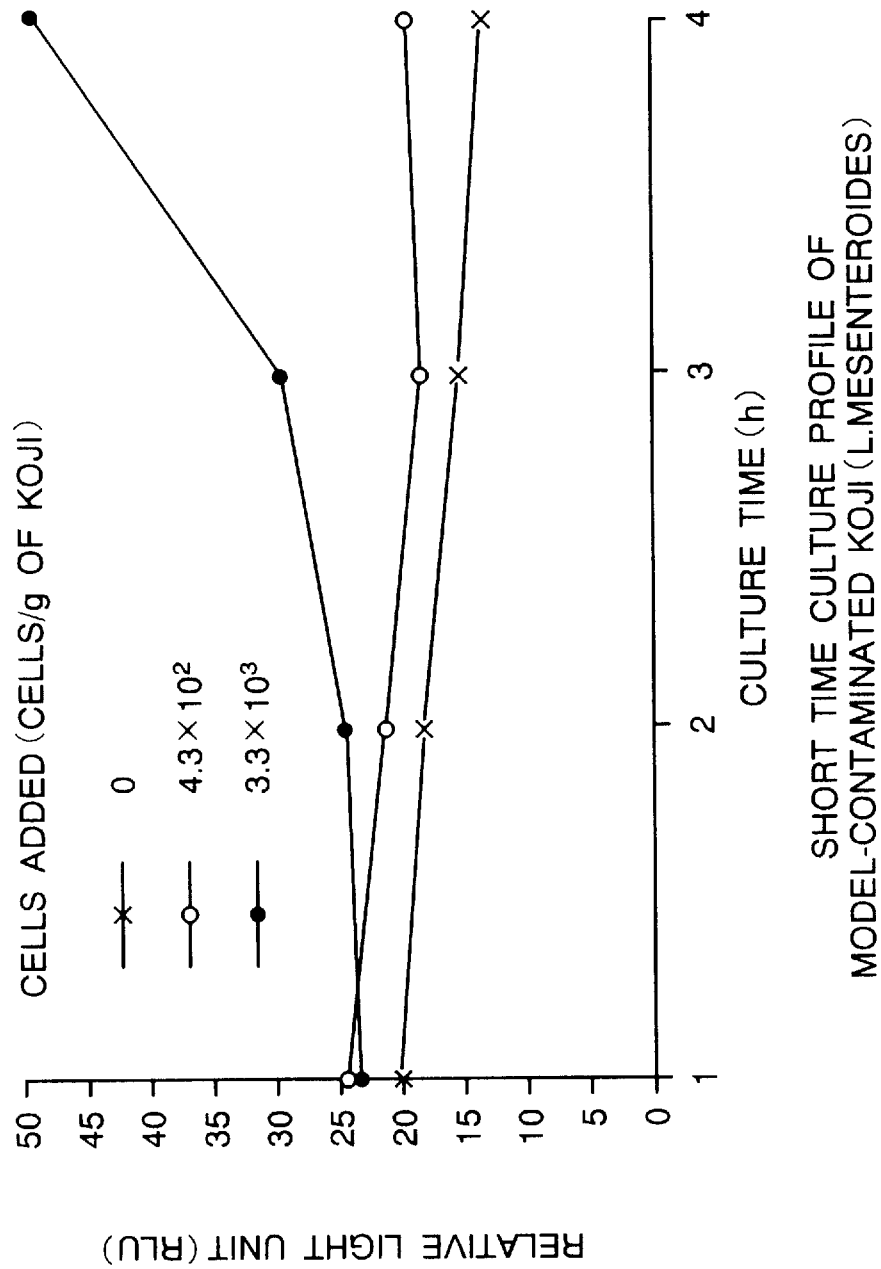
FIG. 13 illustrates the result of the quantitative determination of lactic acid bacteria in koji for soy sauce contaminated with the lactic acid bacteria.

The results are shown in FIG. 13.

It has been revealed from the results of FIGS. 12 and 13 that relative light unit will not be substantially increased in the portions of *Bacillus subtilis* and lactic acid bacteria contaminating soya koji in the initial concentration of $5 \times 10^2$/g koji and $4.3 \times 10^2$/g koji, respectively, even after 4 hours.

In contrast, relative light unit is substantially increased in the portions of the bacteria contaminating soya koji in the initial concentration of $5 \times 10^3$/g koji and $3.3 \times 10^3$/g koji, respectively, after 4 hours.

The initial concentration of the contaminant bacteria (*Batillus subtilis* and lactic acid bacteria) in the materials charged in soya koji can be quantitatively measured approximately.

EXAMPLE 18
(Method for quantitatively determining various germs in soya koji contaminated therewith)

A material for preparing koji was prepared by mixing boiled and skimmed soy beans with roasted and smashed wheat according to the conventional method for preparing soya koji.

A seed koji for soya sauce was inoculated in the material, and a suspension of various germs isolated from domestic waste water (viable cells $10^9$/ml) was sprayed uniformly to obtain a material for preparing koji contaminated with various germs.

Figure 14:
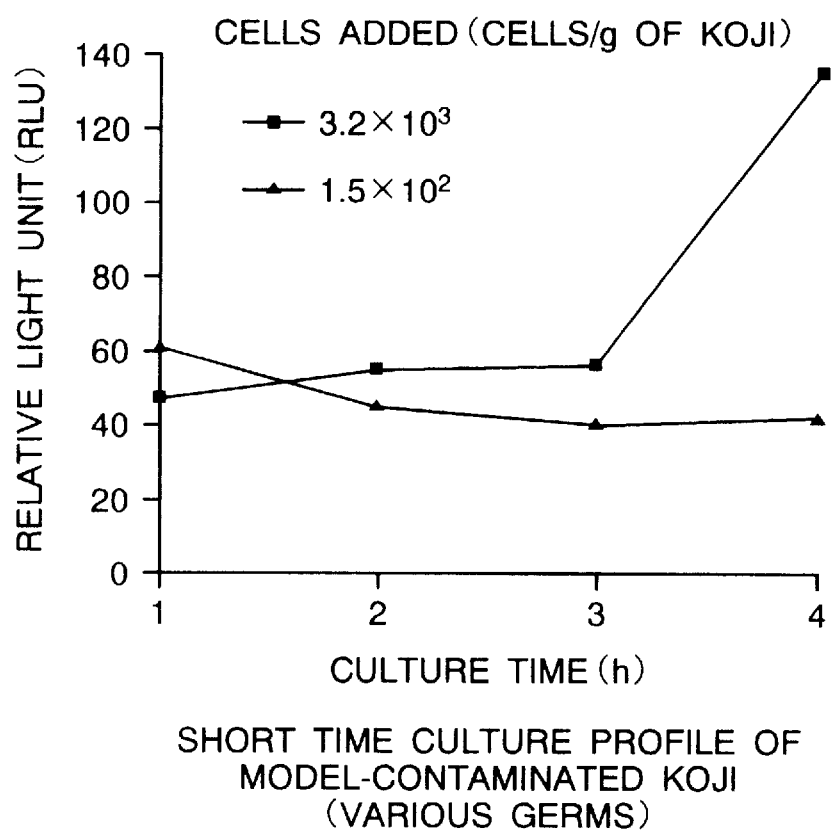
FIG. 14 illustrates the result of the quantitative determination of various germs in materials having charged thereinto koji for soy sauce contaminated with the the various germs.

This material was the material for preparing koji containing various germs (counts/g koji) described in FIG. 14.

Next, the various germs were quantitatively measured in the same manner as the method for quantitatively determining *Bacillus subtilis* in soya koji contaminated therewith in Example 16 except that soya koji contaminated with *Bacillus subtilis* was replaced by the material for preparing koji contaminated with various germs.

The result is shown in FIG. 14.

It is proved from the result in FIG. 14 that approximate count of various germs at initiation of preparing koji can be estimated.

That is, relative luminescence is little increased even after 4 hours in the material having a concentration of various germs contaminating the material of $1.5 \times 10^2$/g of material, while it is increased substantially after 4 hours in the material having a concentration of various germs contaminating the material of $3.2 \times 10^3$/g of material. It is thus revealed that various germs in the initial material for preparing koji can be approximately determined quantitatively.

EXAMPLE 19
(Method for measuring the amount of ATP per CFU of *Saccharomyces cerevisiae*)

The following steps were carried out in this sequence to measure the amount of ATP per CFU of *Saccharomyces cerevisiae*:

step 1: preparation of the culture solution of *Saccharomyces cerevisiae* as a subject microorganism;

step 2: elimination of free ATP from the culture solution;

step 3: preparation of a phosphate buffer for dilution of the culture solution of the subject microorganism;

step 4: preparation of a suspension of the subject microorganism;

step 5: measurement of luminescence of free ATP in the suspension of the subject microorganism;

step 6: addition of an ATP extracting agent to the diluted suspension of the subject microorganism and measurement of luminescence of the total ATP consisting of free ATP which is present before addition of the extracting agent and the extracted ATP after addition of the extracting agent;

step 7: calculation of the amount of luminescence of ATP in the cells;

step 8: calculation of the corrected amount of luminescence of ATP in the cells;

step 9: calculation of the concentration of ATP corresponding to the corrected amount of luminescence;

step 10: calculation of CFU per ml of the suspension of the subject microorganism by the pour culture method;

step 11: measurement of the amount of ATP per CFU.

Step 1: Preparation of the culture solution of *Saccharomyces cerevisiae* as a subject microorganism;

In 8 ml of a YM medium (1% glucose, 0.5% peptone, 0.3% yeast extract, 0.3% malt extract, pH 6.0) was inoculated *Saccharomyces cerevisiae* NISL Y-3398 in one platinum loop amount and stationary-cultured at 35° C. overnight to obtain a culture solution.

Step 2: Elimination of free ATP from the culture solution of the subject microorganism To 2 ml of the culture solution (containing a large amount of viable cells) obtained in the preceding step were added apyrase and adenosine phosphate deaminase so that the final concentrations are 0.05 U/ml, respectively, and the mixture was treated at 35° C. for 30 minutes in order to eliminate preliminarily free ATP in the culture solution.

The blank level of ATP can be lowered by the treatment.

Step 3: Preparation of a phosphate buffer for dilution of the culture solution of the subject microorganism A phosphate buffer 0.625 mM $KH_2PO_4$ (pH 7.2) was sterilized by heating in an autoclave to prepare a dilution of the culture solution obtained in the preceding step in which free ATP had been eliminated (referred to hereinafter as phosphate buffer).

Step 4: Preparation of a suspension of the subject microorganism

The culture solution in which free ATP had been eliminated was diluted with the phosphate buffer for dilution to prepare a 100,000 times diluted suspension of the subject microorganism *Saccharomyces cerevisiae*. The dilution was left standing 25° C. for 30 minutes before use as the sample for measuring luminescence.

Step 5: Measurement of luminescence of free ATP in the suspension of the subject microorganism To 100 μl of the 100,000 times diluted suspension of the subject microorganism was added 100 μl of super pure water, followed by 100 μl of the luminescent reagent, and the mixture was subjected to the measurement of luminescence with LUMITESTER K-100 (KIKKOMAN) in order to determine the amount of luminescence.

The amount of luminescence of free ATP (referred to hereinafter as free luminescence amount F) in the diluted suspension of the subject microorganism is determined by this measurement.

Step 6: Addition of an ATP extracting agent to the diluted suspension of the subject microorganism and measurement of luminescence of the total ATP consisting of free ATP which is present before addition of the extracting agent and the extracted ATP To 100 μl of a 100,000 times dilution of the subject microorganism suspension was added 100 μl of the ATP extracting reagent (KIKKOMAN), followed by 100 μl of the luminescent reagent after 20 seconds at room temperature, and the mixture was subjected to the measurement of luminescence with LUMITESTER K-100 (KIKKOMAN) in order to determine the amount of luminescence. The amount of luminescence of the total ATP (T) of the free ATP and ATP extracted from the microorganism cells by the action of the extracting agent was determined by this method.

Step 7: Calculation of the amount of luminescence of ATP in the cells

The amount of luminescence of ATP in the cells (T-F) is determined correctly by subtracting the free luminescence amount (F) from the total amount of luminescence (T).

Step 8: Calculation of the corrected amount of luminescence of ATP in the cells

The luciferin-luciferase luminescence reaction described above is inhibited somewhat by ingredients contained in a subject microorganism suspension, and must be corrected in order to determine the amount of luminescence without luminescence inhibition.

That is, 100 μl of $2 \times 10^{-10}$ M ATP standard solution was added to 100 μl of the subject microorganism suspension, followed by 100 μl of the luminescent reagent after 20 seconds, and the amount of luminescence was measured with LUMITESTER K-100 (KIKKOMAN) to determine the amount of internal standard luminescence H.

Next, the amount of luminescence was measured to determine the amount of true standard luminescence G in the same manner as the method for determining the above described amount of internal standard luminescence except that 100 μl of sterile super pure water was used in place of 100 μl of the subject microorganism suspension.

Then, luminescence Y (corrected value) of intracellular ATP in case of having no luminescence inhibition was determined from the following calculation formula:

$Y=(T-F)/K$, $K=(H-F)/G$ herein H: internal standard luminescence amount

F: free luminescence amount

G: ture standard luminescence amount

K: rate of luminescence

T-F: luminescence amount of intracellular ATP obtained in the previous step

T: total luminescence amount.

Step 9: Calculation of the concentration of ATP corresponding to the corrected amount of luminescence The concentration of ATP corresponding to the (corrected) amount of luminescence of ATP in the cells in the absence of luminescence inhibition was determined according to the calibration curve shown in FIG. 10 which had been prepared preliminarily.

Step 10: Calculation of CFU per ml of the subject microorganism suspension by the pour culture method The subject microorganism suspension was diluted with a sterile YM medium to an appropriate concentration, plated to a sterile plate containing 2% agar, and cultured at 35° C. overnight. The appearing colonies were counted to estimate CFU per ml of the subject microorganism suspension in consideration of the dilution.

Step 11: Measurement of the amount of ATP per CFU

The amount of ATP per CFU of *Saccharomyces cerevisiae* was determined by dividing the concentration of ATP (mole/ml) corresponding to the (corrected) amount of luminescence of ATP in the cells in the absence of luminescence inhibition by CFU per ml of the subejct microorganism suspension obtained in step 10 (CFU/ml).

As a result, the amount of ATP of $3.07 \times 10^{-16}$ mole/CFU was obtained.

This result is slightly different from the result of the previous Example 11 ($1.21 \times 10^{-16}$ mole/CFU), but it is believed due to the difference of the diluted suspensions.

The results described above are shown in Table 8.

| The amount of ATP per CFU of *Saccharomyces cerevisiae* (mole/CFU) | |
|---|---|
| Dilution | 100,000 times |
| Total luminescence (T) | 5,506 |
| Free luminescence (F) | 91 |
| T - F luminescence | 5,415 |
| Corrected luminescence | 5,471 |
| ATP concentration (mole/ml) | $8.94 \times 10^{-14}$ |
| Experimental value (pour culture method) (CFU/ml) | $2.91 \times 10^2$ |
| Amount of ATP (mole/CFU) | $3.07 \times 10^{-16}$ |

The amount of ATP per CFU of the subject microorganism *Saccharomyces cerevisiae* can be easily determined from the result in Table 8 according to the present invention.

EXAMPLE 20

(Method for measuring the viable cells of *Saccharomyces cerevisiae* in tomato ketchup)

The following steps were carried out in this sequence to measure the concentration of *Saccharomyces cerevisiae* in tomato ketchup:

step 1: preparation of the diluted suspension of tomato ketchup containing *Saccharomyces cerevisiae* as a subject microorganism;

step 2: elimination of free ATP from the diluted tomato ketchup suspension;

step 3: measurement of luminescence of free ATP in the diluted tomato ketchup suspension in which free ATP has been eliminated;

step 4: addition of an ATP extracting agent to the diluted tomato ketchup suspension in which free ATP has been eliminated and measurement of luminescence of the total ATP consisting of a trace amount of free ATP and the extracted ATP after addition of the extracting agent;

step 5: measurement of the amount of luminescence of ATP extracted from the cells;

step 6: calculation of the corrected amount of luminescence of ATP;

step 7: calculation of the concentration of ATP corresponding to the corrected amount of luminescence;

step 8: calculation of CFU per ml of the diluted tomato ketchup suspension containing *Saccharomyces cerevisiae*;

step 9: comparative example (calculation of CFU per ml of the diluted tomato ketchup suspension containing *Saccharomyces cerevisiae* by the pour culture method).

Step 1: Preparation of the diluted suspension of tomato ketchup containing *Saccharomyces cerevisiae* as a subject microorganism;

8 $\mu$l of a culture solution of *Saccharomyces cerevisiae* diluted 10 times with a phosphate buffer (diluent) was added to 2.0 g of a commercially available tomato ketchup, followed by 18 ml of additional diluent, and the mixture was mixed homogeneously.

Next, a 1 ml of portion of the mixture was taken out, to which 19 ml of the diluent was added, and the mixture was mixed homogeneously to prepare a 200 times dilution of tomato ketchup containing the subject microorganism.

Step 2: Elimination of free ATP from the diluted tomato ketchup suspension

To the diluted tomato ketchup suspension were added apyrase and adenosine phosphate deaminase so that the final concentrations are 0.05 U/ml, respectively, and the mixture was treated at 25° C. for 30 minutes in order to prepare a diluted tomato ketchup suspension from which free ATP had been eliminated.

As a comparison, free ATP was eliminated in the same manner as above except that the combination of apyrase and adenosine phosphate deaminase was replaced by apyrase alone.

Figure 15:
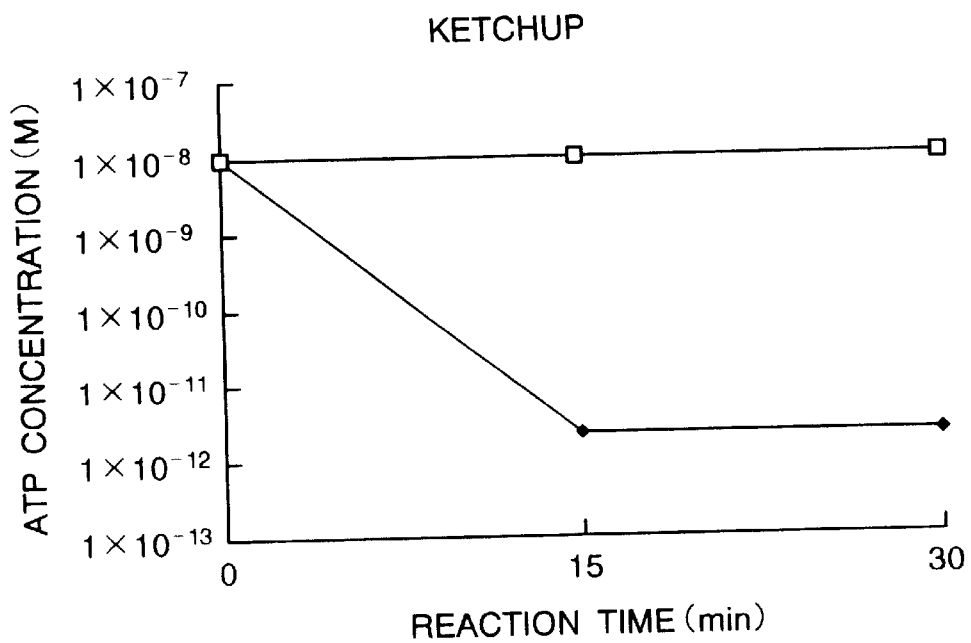
FIG. 15 illustrates the relationship between the reaction time and the concentration of ATP in the elimination of free ATP in diluted suspensions of tomato ketchups contaminated with yeast by the addition of adenosine phosphate deaminase in combination with apyrase.

The results are shown in FIG. 15.

It is revealed from the result of FIG. 15 that apyrase alone cannot eliminate the free ATP in the diluted tomato ketchup suspension, but the combination of apyrase and adenosine phosphate deaminase can lower the initial concentration of free ATP in the diluted suspension to a level of about $\frac{1}{10,000}$.

Step 3: Measurement of luminescence of free ATP in the diluted tomato ketchup suspension in which free ATP has been eliminated.

To 100 $\mu$l of the diluted tomato ketchup suspension from which free ATP had been eliminated were added 100 $\mu$l of sterile super pure water and 100 $\mu$l of the luminescent reagent, and the mixture was subjected to the measurement of luminescence of ATP with a LUMITESTER K-100 (KIKKOMAN).

The amount of luminescence of the trace amount of the free ATP (F) can be determined by this measurement.

Step 4: Addition of an ATP extracting agent to the diluted tomato ketchup suspension from which free ATP had been eliminated and measurement of luminescence of the total ATP consisting of the trace amount of free ATP and the extracted ATP from the cells (ATP in the cells)

To 100 $\mu$l of a diluted tomato ketchup suspension was added 100 $\mu$l of the ATP extracting reagent (KIKKOMAN), followed by 100 $\mu$l of the luminescent reagent after 20 seconds at room temperature, and the mixture was subjected to the measurement of luminescence with LUMITESTER K-100 (KIKKOMAN).

The amount of luminescence of the total ATP (T) of the trace amount of free ATP in the suspension and ATP extracted from the cells (ATP in the cells) can be determined by this method.

Step 5: Measurement of the amount of luminescence of ATP extracted from the cells The amount of luminescence of ATP extracted from the cells (T-F) is determined correctly by subtracting the free luminescence amount F from the total amount of luminescence T.

Step 6: Calculation of the corrected amount of luminescence

The luciferin-luciferase luminescence reaction described above is inhibited somewhat by ingredients contained in the suspension, and must be corrected in order to determine the amount of luminescence without luminescence inhibition.

That is, 100 $\mu$l of $2\times10^{-10}$M ATP standard solution was added to 100 $\mu$l of the suspension, followed by 100 $\mu$l of the luminescent reagent after 20 seconds, and the amount of luminescence was measured with LUMITESTER K-100 (KIKKOMAN) to determine the amount of internal standard luminescence H.

Next, the amount of true standard luminescence G was measured in the same manner as the method for determining the above described amount of internal standard luminescence H except that 100 $\mu$l of sterile super pure water was used in place of 100 $\mu$l of the suspension.

Then, luminescence Y (corrected value) of intracellular ATP in case of having no luminescence inhibition was determined from the following calculation formula:

$$Y=(T-F)/K,$$

$$K=(H-F)/G$$

herein H: internal standard luminescence amount

F: free luminescence amount

G: true standard luminescence amount

K: rate of luminescence

T-F: luminescence amount of intracellular ATP obtained in the previous step

T: total luminescence amount.

Step 7: Calculation of the concentration of ATP corresponding to the corrected amount of luminescence The concentration of ATP corresponding to the (corrected) amount of luminescence of ATP in the cells in the absence of luminescence inhibition was determined according to the calibration curve shown in FIG. 10 which had been prepared preliminarily.

Step 8: Calculation of CFU per ml of the diluted tomato ketchup suspension containing *Saccharomyces cerevisiae*

The concentration of ATP corresponding to the corrected amount of luminescence obtained in step 7 of this example was divided by the amount of ATP per CFU of *Saccharomyces cerevisiae*, $3.07\times10^{-16}$ mole obtained in step 11 (final step) in Example 19 to calculate the CFU concentration per ml of the diluted tomato ketchup suspension containing *Saccharomyces cerevisiae*. That is, the result of estimating the viable cells of *Saccharomyces cerevisiae* in tomato ketchup was obtained.

Step 9: Comparative Example (Calculation of CFU per ml of the diluted tomato ketchup suspension containing *Saccharomyces cerevisiae*)

The diluted tomato ketchup suspension containing *Saccharomyces cerevisiae* was diluted appropriately with a YM medium, plated to a YM medium containing agar by the pour culture method, and cultured at 35° C. for 24 hours. The appearing colonies were counted to estimate CFU per ml of the diluted suspension in consideration of the dilution.

The concentration of the viable cells thus obtained is regarded as the observed value obtained by the pour culture method (CFU/ml).

The results described above are shown in Table 9.

TABLE 9

Measurement of the viable cells of *Saccharomyces cerevisiae* in tomato ketchup (mole/CFU)

| Dilution | 200 times |
|---|---|
| Total luminescence (T) | 1,332 |
| Free luminescence (F) | 107 |
| T − F luminescence | 1,225 |
| Corrected luminescence | 1,734 |
| ATP concentration (mole/ml) | $2.83 \times 10^{-14}$ |
| Calculated value (Present Example) (CFU/ml) | $9.23 \times 10$ |
| Observed value (pour culture method) (CFU/ml) | $8.15 \times 10$ |
| Calculated value (Present Example) (CFU/g) | $1.85 \times 10^4$ |
| Observed value (pour culture method) (CFU/g) | $1.63 \times 10^4$ |

The concentration of viable cells of the diluted tomato ketchup suspension containing *Saccharomyces cerevisiae* from the result in Table 9 according to the present invention is 9.23×10 CFU/ml, which is comparable to 8.15×10 CFU/ml obtained by the pour culture method which has been conventionally believed to have the highest precision and high reliability of measurement.

It is also revealed that the viable cells of *Saccharomyces cerevisiae* in 1 g of the tomato ketchup is 1.85×10$^4$, which is obtained by multiplying the concentration of the viable cells (calculated) by the dilution rate, 200 times.

It is thus revealed that the viable cells of *Saccharomyces cerevisiae* in the tomato ketchup can be rapidly measured.

EXAMPLE 21
(Elimination of free ATP in a diluted apple juice suspension contaminated with *Saccharomyces cerevisiae*)

A diluted apple juice suspension contaminated with *Saccharomyces cerevisiae* was prepared in the same manner as the method in Example 20 (Method for measuring the concentration of the viable cells of *Saccharomyces cerevisiae* in tomato ketchup) except that the tomato ketchup was replaced by a 100% apple juice suspension, and step 1 "preparation of the diluted suspension of tomato ketchup containing *Saccharomyces cerevisiae* as a subject microorganism" was replaced by the followings.

"Step 1: preparation of the diluted suspension of tomato ketchup containing *Saccharomyces cerevisiae* as a subject microorganism. A 5 µl portion of a *Saccharomyces cerevisiae* culture solution was added to and mixed homogeneously with 5 ml of a commercially available 100% apple juice suspension. To 1 ml of the mixture taken out was added 19 ml of a diluent (phosphate buffer) to prepare a 20 times dilution of an apple juice suspension contaminated with *Saccharomyces cerevisiae*."

To the diluted apple juice suspension were added apyrase and adenosine phosphate deaminase so that the final concentrations are 0.05 U/ml, respectively, and the mixture was treated at 25° C. for 35 minutes in order to eliminate the free ATP.

As a comparison, the free ATP was eliminated in the same manner as above except that the combination of apyrase and adenosine phosphate deaminase was replaced by apyrase alone in the final concentration of 0.05 U/ml.

Figure 16:
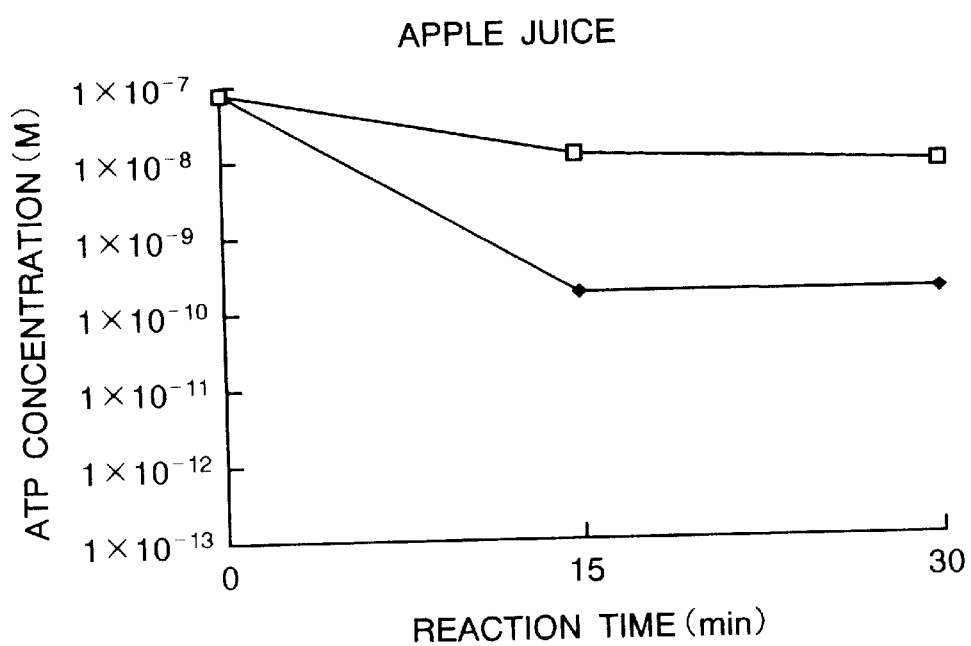
FIG. 16 illustrates the relationship between the reaction time and the concentration of ATP in the elimination of free ATP in diluted suspensions of apple juices contaminated with yeast by the addition of adenosine phosphate deaminase in combination with apyrase.

The results are shown in FIG. 16.

It is revealed from the result of FIG. 16 that the portion to which apyrase is added alone in Comparative Example can eliminate the free ATP only in a little amount from the apple juice, the portion to which the combination of apyrase and adenosine phosphate deaminase is added according to the present invention can lower the concentratio of the initial free ATP in the apple juice to a level of about one several millionth.

EXAMPLE 22
(Measurement of the concentration of the viable cells of *Saccharomyces cerevisiae* in an apple juice)

A diluted apple juice suspension containing the subject microorganism was prepared in the same manner as the method in Example 20 "Method for measuring the concentration of the viable cells of *Saccharomyces cerevisiae* in tomato ketchup" except that the tomato ketchup was replaced by a 100% apple juice suspension, and step 1 was replaced by the followings.

"Step 1: preparation of the diluted suspension of apple juice containing *Saccharomyces cerevisiae* as a subject microorganism. A 5 µl portion of a *Saccharomyces cerevisiae* culture solution was added to and mixed homogeneously with 5 ml of a commercially available 100% apple juice suspension. To 1 ml of the mixture taken out was added 19 ml of a diluent (phosphate buffer) to prepare a 20 times dilution of an apple juice suspension contaminated with *Saccharomyces cerevisiae*."

The concentration of the viable cells of *Saccharomyces cerevisiae* in the apple juice was measured.

The results are shown in Table 10.

TABLE 10

Measurement of the viable cells of *Saccharomyces cerevisiae* in apple juice (mole/CFU)

| Dilution | 20 times |
|---|---|
| Total luminescence (T) | 21,175 |
| Free luminescence (F) | 4,182 |
| T − F luminescence | 16,993 |
| Corrected luminescence | 46,340 |
| ATP concentration (mole/ml) | $7.57 \times 10^{-13}$ |
| Calculated value (Present Example) (CFU/ml) | $2.47 \times 10^3$ |
| Observed value (pour culture method) (CFU/ml) | $1.47 \times 10^3$ |
| Calculated value (Present Example) (CFU/g) | $4.93 \times 10^4$ |
| Observed value (pour culture method) (CFU/g) | $2.94 \times 10^4$ |

The concentration of viable cells of the 20 times dilution of the apple juice suspension containing *Saccharomyces cerevisiae* (CFU/ml) from the result in Table 10 according to the present invention is 2.47×10$^3$, which is comparable to 1.47×10$^3$ obtained by the pour culture method which has been conventionally believed to have the highest precision as well as reliability of measurement.

It is also revealed that the viable cells of *Saccharomyces cerevisiae* in 1 g of the apple juice is 4.93×10$^4$, which is obtained by multiplying the concentration of the viable cells (calculated) by the dilution rate, 20 times.

It is thus revealed that the viable cells of *Saccharomyces cerevisiae* in the apple juice can be rapidly measured.

EXAMPLE 23
(Elimination of free ATP in a bean curd suspension contaminated with various germs)

A diluted silk-strained bean curd suspension contaminated with various germs was prepared in the same manner as the method in Example 20 (Method for measuring the concentration of the viable cells of *Saccharomyces cerevisiae* in tomato ketchup) except that the tomato ketchup was replaced by a commercially available silk-strained bean curd, and step 1 was replaced by the followings.

"Step 1: preparation of the diluted suspension of silk-strained bean curd containing various germs.

A commercially available fresh "silk-strained bean curd" was mixed with an appropriate amount of a germ suspension which had been preliminarily separated from domestic waste water to give a bean curd contaminated with various germs. To 10 g of the bean curd was added 90 ml of a phosphate buffer (diluent) and pressed with a crusher "STOMACHER 400-T (Organo)" to prepare a diluted suspension of bean curd. To a 1 ml portion of the suspension was added 39 ml of the diluent, and the mixture was homogeneously stirred to prepare finally a 400 times diluted bean curd suspension.

To the diluted bean curd suspension were added apyrase and adenosine phosphate deaminase so that the final concentrations are 0.05 U/ml, respectively, and the mixture was treated at 25° C. for 35 minutes in order to eliminate the free ATP.

Figure 17:
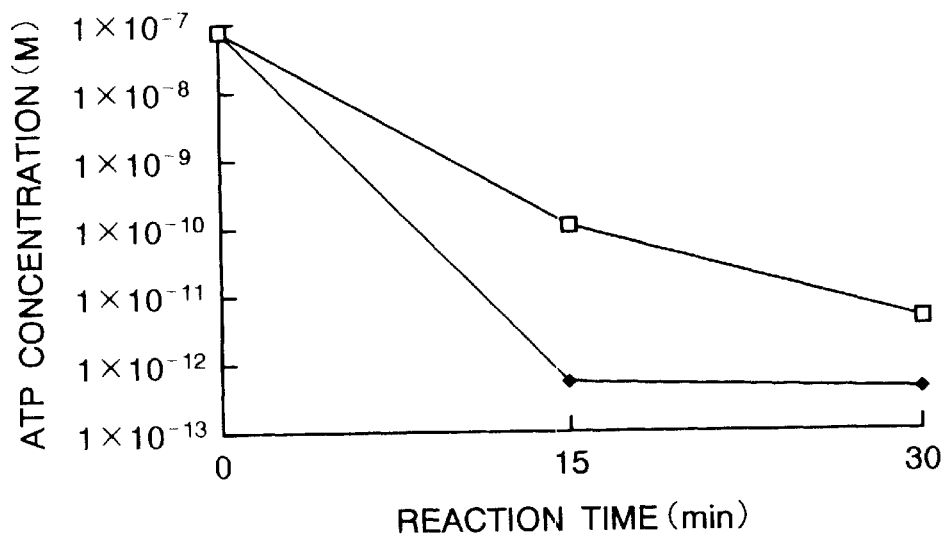
FIG. 17 illustrates the relationship between the reaction time and the concentration of ATP in the elimination of free ATP in diluted suspensions of bean curds contaminated with various germs by the addition of adenosine phosphate deaminase in combination with apyrase.

The results are shown in FIG. 17.

It is revealed from the result of FIG. 17 that the portion to which apyrase is added alone in Comparative Example can eliminate the free ATP to a level of about one ten thousandth, while the portion to which the combination of apyrase and adenosine phosphate deaminase is added according to the present invention can lower the concentration of the initial free ATP to a level of about one several hundred thousandth.

EXAMPLE 24
(Measurement of the concentration of the viable cells of contaminant germs in bean curd)

A silk-strained bean curd contaminated with various germs was prepared in the same manner as the method in Example 20 "Method for measuring the concentration of the viable cells of *Saccharomyces cerevisiae* in tomato ketchup" except that the tomato ketchup was replaced by a silk-strained bean curd, and step 1 was replaced by the followings.

"Step 1: preparation of a diluted silk-strained bean curd suspension contaminated with various germs A commercially available fresh "silk-strained bean curd" was mixed with an appropriate amount of a germ suspension which had been preliminarily separated from domestic waste water to give a bean curd contaminated with various germs. To 10 g of the bean curd was added 90 ml of a phosphate buffer (diluent) and pressed with a crusher "STOMACHER 400-T (Organo)" to prepare a diluted suspension of bean curd. To a 1 ml portion of the suspension was added 39 ml of the diluent, and the mixture was homogeneously stirred to prepare finally a 400 times diluted bean curd suspension.

The concentration of the viable cells of various germs in silk-strained bean curd was measured.

The results are shown in Table 11.

(1) The observed value given in Table 11 is determined by the following procedure.
(Calculation of CFU per ml of the subject microorganism suspension by the pour culture method)

The subject microorganism suspension was diluted appropriately with a sterile "standard liquid medium", plated to a sterile "standard agar medium" containing 2% agar, and cultured at 35° C. for 2 days. The appearing colonies were counted to estimate CFU per ml of the diluted suspension in consideration of the dilution.

(2) The number of the viable cells in the diluted subject microorganism suspension was determined by dividing the amount of ATP in the viable cells by the amount of ATP per CFU obtained preliminarily, and in this example the concentration of the viable cells in the bean curd was determined with use of the amount of ATP per CFU of general viable bacteria, $3 \times 10^{-18}$ mole/CFU.

The result is shown in Table 11.

TABLE 11

| Measurement of the various bacteria in bean curd | |
|---|---|
| Dilution | 400 times |
| Total luminescence (T) | 3,325 |
| Free luminescence (F) | 49 |
| T – F luminescence | 3,276 |
| Corrected luminescence | 5,164 |
| ATP concentration (mole/ml) | $7.79 \times 10^{-14}$ |
| Calculated value (Present Example) (CFU/ml) | $2.60 \times 10^4$ |
| Observed value (pour culture method) (CFU/ml) | $2.32 \times 10^4$ |
| Calculated value (Present Example) (CFU/g) | $1.04 \times 10^7$ |
| Observed value (pour culture method) (CFU/g) | $9.28 \times 10^6$ |

The concentration (calculated) of viable cells in the 400 times diluted suspension contaminated with various germs (CFU/ml) according to the present invention from the result in Table 11 is $2.60 \times 10^4$, which is comparable to $2.32 \times 10^4$ obtained by the pour culture method which has been conventionally believed to have the highest precision and reliability of measurement. It is also revealed that the viable cells of the contaminant bacteria in 1 g of the bean curd is $1.04 \times 10^7$, which is obtained by multiplying the concentration of the viable cells (calculated) by the dilution rate, 400 times.

EXAMPLE 25
(Elimination of ATP in a crab leg meat like boiled fish paste contaminated with various germs)

A diluted crab leg meat like boiled fish paste suspension contaminated with various germs was prepared in the same manner as the method in Example 20 (Method for measuring the concentration of the viable cells of *Saccharomyces cerevisiae* in tomato ketchup) except that the tomato ketchup was replaced by a crab leg meat like boiled meat paste suspensions and step 1 was replaced by the followings.

"Step 1: preparation of the diluted suspension of crab leg meat like boiled fish paste contaminated with a subject microorganism.

A crab leg meat like boiled fish paste contaminated with various germs was obtained by spraying a commercially available "crab leg meat like boiled fish paste" with an appropriate amount of a suspension various germs which had been preliminarily isolated from domestic waste water. To 10 g of the paste was added 90 ml of a phosphate buffer as a diluent, and the mixture was broken with a press-crusher "STOMACHER 400-T (Organo) to prepare a diluted suspension of crab leg fish like boiled fish paste. To 1 ml of the supernatant of the suspension was added 9 ml of the diluent, and the mixture was mixed homogeneously to prapare finally a 100 times diluted suspension of crab leg meat like boiled fish paste.

To the diluted suspension were added apyrase and adenosine phosphate deaminase so that the final concentrations are 0.05 U/ml, respectively, and the mixture was treated at 25° C. for 30 minutes in order to eliminate the free ATP.

Figure 18:
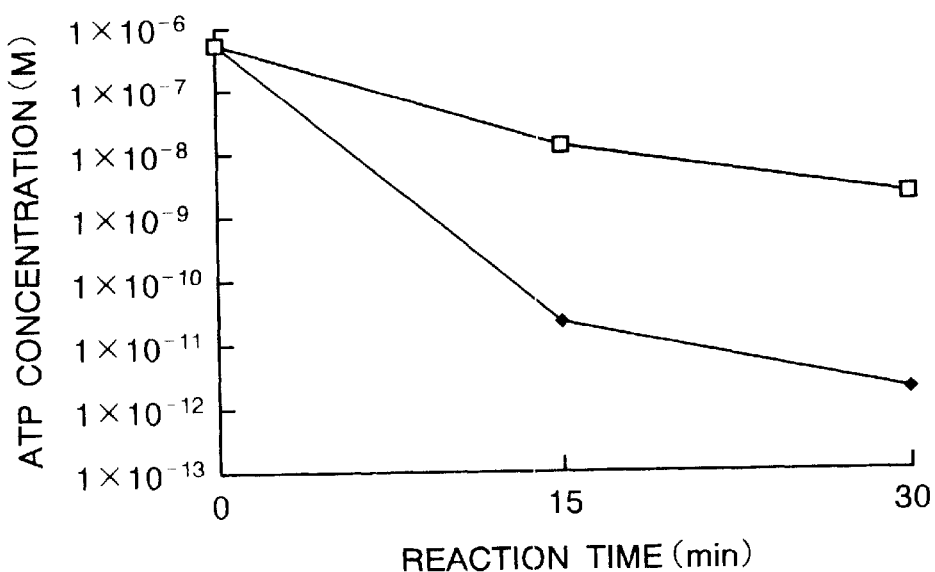
FIG. 18 illustrates the relationship between the reaction time and the concentration of ATP in the elimination of free ATP in diluted suspensions of boiled crab leg meat like fish pastes contaminated with various germs by the addition of adenosine phosphate deaminase in combination with apyrase.

The results are shown in FIG. 18.

It is revealed from the result of FIG. 18 that the portion to which apyrase is added alone in Comparative Example can eliminate the free ATP of the suspension only insufficiently, the portion to which the combination of apyrase and adenosine phosphate deaminase is added according to the present invention can lower the concentration of the initial free ATP to a level of about one several hundred thousandth.

EXAMPLE 26

(Measurement of the concentration of the viable cells of contaminant bacteria in crab leg meat like boiled fish paste)

A diluted crab leg meat like boiled fish paste suspension contaminated with various germs was prepared in the same manner as the method in Example 20 (Method for measuring the concentration of the viable cells of *Saccharomyces cerevisiae* in tomato ketchup) except that the tomato ketchup was replaced by a crab leg meat like boiled fish paste suspension, and step 1 was replaced by the followings.

"Step 1: preparation of the diluted suspension of crab leg fish meat boiled fish paste contaminated with a subject microorganism.

A crab leg meat like boiled fish paste contaminated with various germs was obtained by spraying a commercially available "crab leg meat like boiled fish paste" with an appropriate amount of a suspension various germs which had been preliminarily isolated from domestic waste water. To 10 g of the paste was added 90 ml of a phosphate buffer as a diluent, and the mixture was broken with a press-crusher "STOMACHER 400-T (Organo) to prepare a diluted suspension of crab leg fish like boiled fish paste. To 1 ml of the supernatant of the suspension was added 9 ml of the diluent, and the mixture was mixed homogeneously to prapare finally a 100 times diluted suspension of crab leg meat like boiled fish paste.

The concentration of the viable cells of various germs in crab leg meat like boiled fish paste as measured.

The results are shown in Table 12.

(1) The observed value given in Table 12 is determined by the following procedure.

(Calculation of CFU per ml of the subject microorganism suspension by the pour culture method)

The subject microorganism suspension was diluted appropriately with a sterile "standard liquid medium", plated to a sterile "standard agar medium" containing 2% agar, and cultured at 35° C. for 2 days. The appearing colonies were counted to estimate CFU per ml of the diluted suspension in consideration of the dilution.

(2) The number of the viable cells in the diluted subject microorganism suspension was determined by dividing the amount of ATP in the viable cells by the amount of ATP per CFU obtained preliminarily, and in this example the concentration of the contaminant viable cells in the crab leg fish like boiled fish paste was determined with use of the amount of ATP per CFU of general viable bacteria, $3 \times 10^{-18}$ mole/CFU.

The result is shown in Table 12.

TABLE 12

Measurement of the various germs in crab leg meat like boiled fish paste

| Dilution | 100 times |
| --- | --- |
| Total luminescence (T) | 5,768 |
| Free luminescence (F) | 81 |

TABLE 12-continued

Measurement of the various germs in crab leg meat like boiled fish paste

| T – F luminescence | 5,687 |
| --- | --- |
| Corrected luminescence | 8,500 |
| ATP concentration (mole/ml) | $1.28 \times 10^{-13}$ |
| Calculated value (Present Example) (CFU/ml) | $4.27 \times 10^4$ |
| Observed value (pour culture method) (CFU/ml) | $6.18 \times 10^4$ |
| Calculated value (Present Example) (CFU/g) | $4.27 \times 10^6$ |
| Observed value (pour culture method) (CFU/g) | $6.18 \times 10^6$ |

The concentration (calculated) of viable cells in the 100 times diluted suspension of the crab leg meat like fish paste contaminated with various germs (CFU/ml) from the result in Table 12 is $4.27 \times 10^4$, which is comparable to the observed value $6.18 \times 10^4$ obtained by the pour culture method which has been conventionally believed to have the highest precision and reliability of measurement.

It is also revealed that the various germs in 1 g of the crab leg meat like fish paste is $4.27 \times 10^6$, which is obtained by multiplying the concentration of the viable cells obtained by the present invention (calculated value) by the dilution rate, 200 times.

It is thus revealed that various germs in the crab leg meat like fish paste can be rapidly measured by the present invention.

EXAMPLE 27

(Elimination of free ATP in a diluted suspension of boiled rice contaminated with various germs)

A diluted suspension of boiled rice contaminated with various germs was prepared in the same manner as the method in Example 20 "Method for measuring the concentration of the viable cells of *Saccharomyces cerevisiae* in tomato ketchup" except that the tomato ketchup was replaced by boiled rice, and step 1 was replaced by the followings.

"Step 1: preparation of the diluted suspension of boiled rice contaminated with various germs.

Ordinary "boiled rice" was divided into many 10 g portions and sprayed with a suspension of bacteria which had been preliminarily isolated from domestic waste water to obtain a boiled rice contaminated with various germs.

A 3 g portion of the boiled rice contaminated with various rice was placed in a sterile plastic tube (internal diameter; 25 mm, length: 110 mm, volume: 50 ml) (FALCON TUBE, Becton Dickinson), followed by 6 ml of phosphate buffer (diluent), and the mixture was shaken artificially for about 1 minute. The supernatant (3 ml) was used as the diluted suspension of boiled rice.

Apyrase and adenosine phosphate deaminase were added to the diluted suspension of boiled rice so that the final concentration is 0.05 U/ml, respectively, and the mixture was reacted at 25° C. for 30 minutes to eliminate the free ATP.

Figure 19:
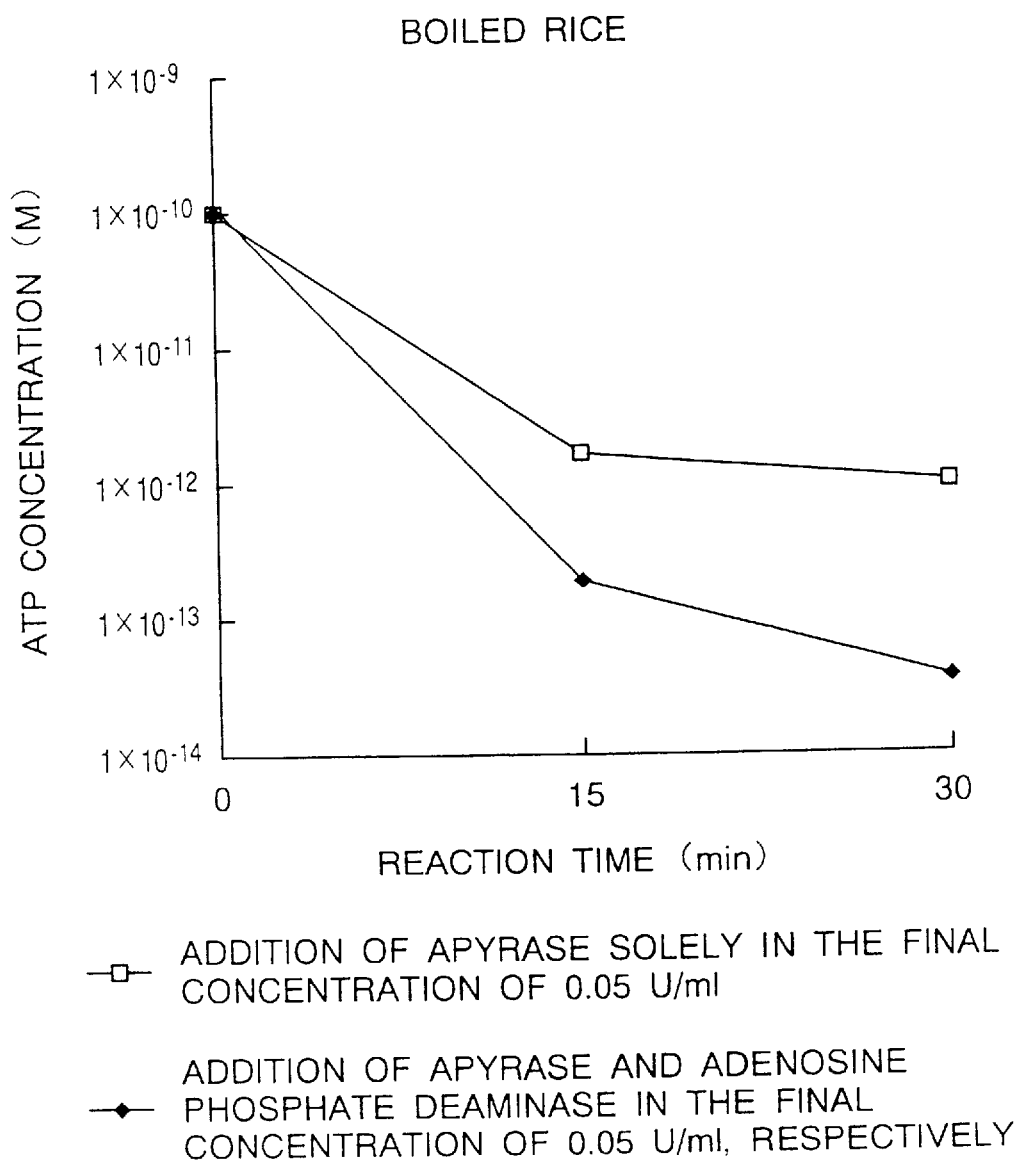
FIG. 19 illustrates the relationship between the reaction time and the concentration of ATP in the elimination of free ATP in diluted suspensions of boiled rice contaminated with various germs by the addition of adenosine phosphate deaminase in combination with apyrase.

The results are shown in FIG. 19.

It is revealed from the result of FIG. 19 that the portion to which apyrase is added alone in Comparative Example can eliminate the free ATP only insufficiently, while the portion to which the combination of apyrase and adenosine phosphate deaminase is added according to the present invention can lower the concentration of the initial free ATP to a level of about one several thousandth.

EXAMPLE 28

(Measurement of the concentration of viable cells of contaminant bacteria in boiled rice)

A diluted suspension of boiled rice contaminated with various germs was prepared in the same manner as the method in Example 20 "Method for measuring the concentration of the viable cells of *Saccharomyces cerevisiae* in tomato ketchup" except that the tomato ketchup was replaced by boiled rice, and step 1 was replaced by the followings.

"Step 1: preparation of the diluted suspension of boiled rice contaminated with various germs.

Ordinary "boiled rice" was divided into many 10 g portions and sprayed with a suspension of bacteria which had been preliminarily isolated from domestic waste water to obtain a boiled rice contaminated with various germs.

A 3 g portion of the boiled rice contaminated with various rice was placed in a sterile plastic tube (internal diameter: 25 mm, length: 110 mm, volume: 50 ml) (FALCON TUBE, Becton Dickinson), followed by 6 ml of a phosphate buffer (diluent), and the mixture was shaken artificially for about 1 minute. The supernatant (3 ml) was used as the diluted suspension of boiled rice.

In addition, it follows that 1 ml of the diluted suspension contains various germs attached to 0.5 g of boiled rice."

Next, the concentration of the viable cells of various germs as the contamitant in the boiled rice. The correlation between the logarithmic level of ATP of various germs per ml of the diluted suspensions of boiled rice (mole/ml) and the logarithmic numbers of various germ cells per g of the boiled rice (log CFU/g) obtained by the pour culture method was examined.

Figure 20:
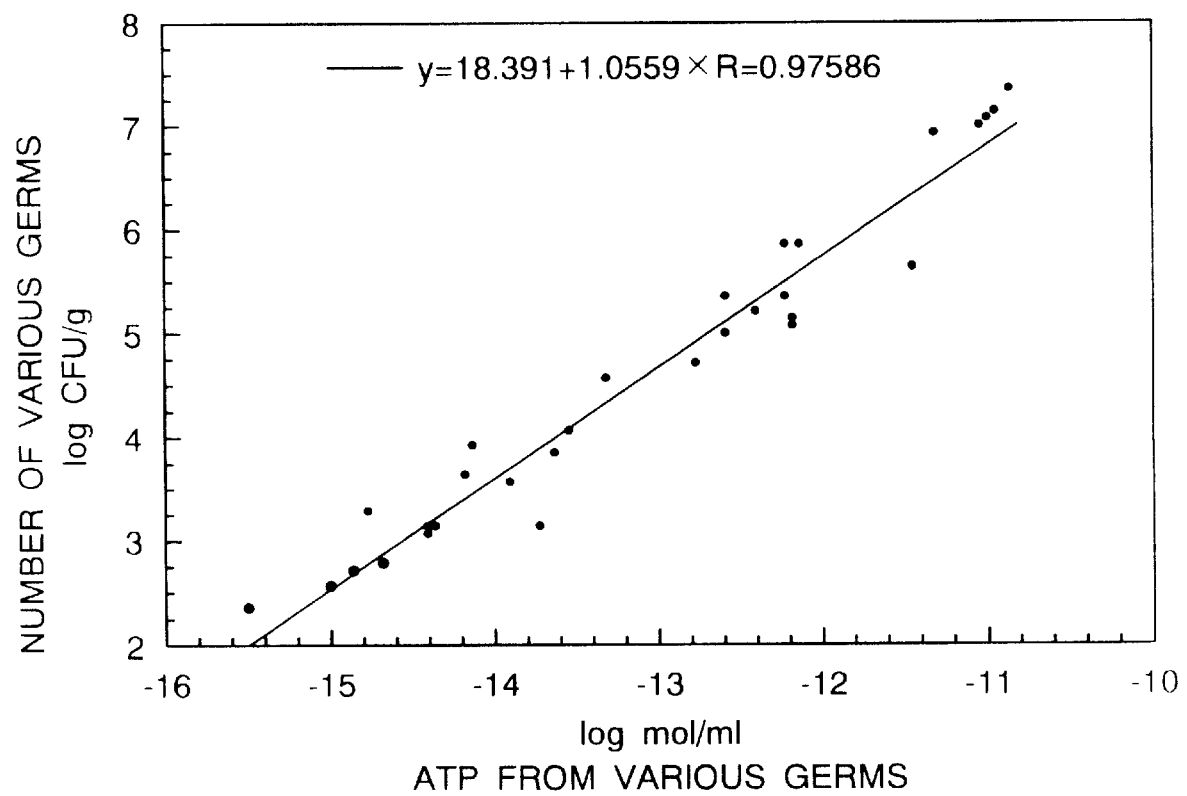
FIG. 20 illustrates the correlation between the logarithmic level of ATP of various germs per ml of the diluted suspensions of boiled rice (mole/ml) and the logarithmic numbers of various germ cells per g of the boiled rice (log CFU/g) obtained by the pour culture method.

The result thus obtained is illustrated in FIG. 20.

(1) The number of various germs by the pour culture method was determined by the following procedure.

(Calculation of CFU per ml of the subject microorganism suspension by the pour culture method)

The subject microorganism suspension was diluted appropriately with a sterile "standard liquid medium", plated to a sterile "standard agar medium" containing 2% agar, and cultured at 35° C. for 2 days. The appearing colonies were counted to estimate CFU per ml of the diluted suspension in consideration of the dilution. The value obtained was then doubled to obtain the various germ cells per g of boiled rice.

It is revealed from the result of FIG. 20 that in the number of various germs of 100 CFU/g or more (i.e. at a division of 2 or more on the Y axis), the level of ATP of various germs per ml of the diluted suspensions of boiled rice on the basis of logarithmic mole/ml and the logarithmic numbers of various germ cells per g of the boiled rice (log CFU/g) obtained by the pour culture method exhibit positive correlation (correlation coefficient: 0.976), and thus various germs in the boiled rice can be quantitatively determined easily and rapidly at good sensitivity.

What is claimed is:

1. A composition for eliminating background ATP in an ATP bioluminescence method, said composition comprising effective concentrations to eliminate background ATP in an ATP-containing sample of adenosine phosphate deaminase and at least one other enzyme selected from the group consisting of apyrase, alkaline phosphatase, acid phosphatase, hexokinase and adenosine triphosphatase.

2. A method for eliminating background ATP in an ATP bioluminescence method from an ATP-containing sample under a liquid reaction system comprising adding an appropriate concentration of a composition comprising adenosine phosphate deaminase and at least one other enzyme selected from the group consisting of apyrase, alkaline phosphatase, acid phosphatase, hexokinase and adenosine triphosphatase.

3. A reagent for measuring biological cells comprising effective concentractions of a composition as defined in claim 1, and an ATP extraction reagent in combination with a luminescent reagent containing liciferan-luciferase.

* * * * *